United States Patent
Jameel et al.

(10) Patent No.: US 10,383,987 B2
(45) Date of Patent: Aug. 20, 2019

(54) SURGICAL SWAB WASHING METHOD AND APPARATUS

(71) Applicant: Swabtech Limited, Manchester (GB)

(72) Inventors: Mohamed Mohideen Mohamed Jameel, Chorley (GB); Sarah Haynes, Cheadle Hulme (GB); James Matthew Corden, Romiley (GB)

(73) Assignee: Swabtech Limited, Manchester (GB)

(*) Notice: Subject to any disclaimer, the term of this patent is extended or adjusted under 35 U.S.C. 154(b) by 672 days.

(21) Appl. No.: 14/423,670

(22) PCT Filed: Aug. 5, 2013

(86) PCT No.: PCT/GB2013/052084
§ 371 (c)(1),
(2) Date: Feb. 24, 2015

(87) PCT Pub. No.: WO2014/029967
PCT Pub. Date: Feb. 27, 2014

(65) Prior Publication Data
US 2015/0283310 A1 Oct. 8, 2015

(30) Foreign Application Priority Data
Aug. 24, 2012 (GB) .................................. 1215097.5

(51) Int. Cl.
*A61M 1/02* (2006.01)
*A61M 1/00* (2006.01)

(52) U.S. Cl.
CPC ........ *A61M 1/0281* (2013.01); *A61M 1/0001* (2013.01); *A61M 2202/0429* (2013.01)

(58) Field of Classification Search
CPC .......................... A61M 1/0281; A61M 1/0001
(Continued)

(56) References Cited

U.S. PATENT DOCUMENTS 4,842,576 A * 6/1989 Lysaght ............. A61M 1/3672
222/101
4,922,922 A 5/1990 Pollock et al.
(Continued)

FOREIGN PATENT DOCUMENTS

CN  200 951 222     9/2007
FR  WO 89/09563    10/1989
(Continued)

OTHER PUBLICATIONS

International Search Report and Written Opinion from PCT/GB2013/052084 dated Dec. 13, 2013.
(Continued)

*Primary Examiner* — Jill A Warden
*Assistant Examiner* — Jacqueline Brazin
(74) *Attorney, Agent, or Firm* — SmithAmundsen LLC

(57) ABSTRACT

Automated methods and apparatus for washing surgical swabs to extract viable red blood cells from said swabs. One method comprises contacting at least one swab retaining viable red blood cells with saline-based wash solution in a receptacle under sterile conditions; and effecting the automated compression and/or agitation of the receptacle containing the swab(s), saline-based wash solution and red blood cells to facilitate extraction of viable red blood cells from the swabs into the saline-based wash solution. Another method comprises providing at least one swab retaining viable red blood cells in a receptacle; providing saline-based wash solution in said receptacle so that it contacts said swab(s) such that viable red blood cells are extracted from the swab(s) into the saline-based wash solution; effecting automated compression and/or agitation of the receptacle containing the swab(s), saline-based wash solution and red blood cells to facilitate extraction of viable red blood cells from the swab(s) into the saline-based wash solution; and
(Continued)

pumping saline-based wash solution containing viable red blood cells extracted from the swab(s) to a reservoir.

16 Claims, 17 Drawing Sheets

(58) Field of Classification Search
USPC .......................................................... 422/536
See application file for complete search history.

(56) References Cited

U.S. PATENT DOCUMENTS

| | | | | |
|---|---|---|---|---|
| 2005/0233352 | A1* | 10/2005 | Zoval | C12Q 1/6806 |
| | | | | 435/6.11 |
| 2007/0163963 | A1* | 7/2007 | Faustman | C12N 5/0087 |
| | | | | 210/695 |
| 2012/0165642 | A1* | 6/2012 | Krensky | A61M 1/0001 |
| | | | | 600/371 |

FOREIGN PATENT DOCUMENTS

| | | |
|---|---|---|
| FR | 2677254 | 12/1992 |
| FR | 2874327 | 2/2006 |
| WO | WO 2012/083412 | 6/2012 |

OTHER PUBLICATIONS

International Prelminary Report on Patentability from PCT/GB2013/052084 dated Feb. 24, 2015.
English Translation of FR 2677254 published Dec. 11, 1992.
English Translation of FR 2874327 published Feb. 24, 2006.
English Translation of CN 200951222 published Sep. 26, 2007.

\* cited by examiner

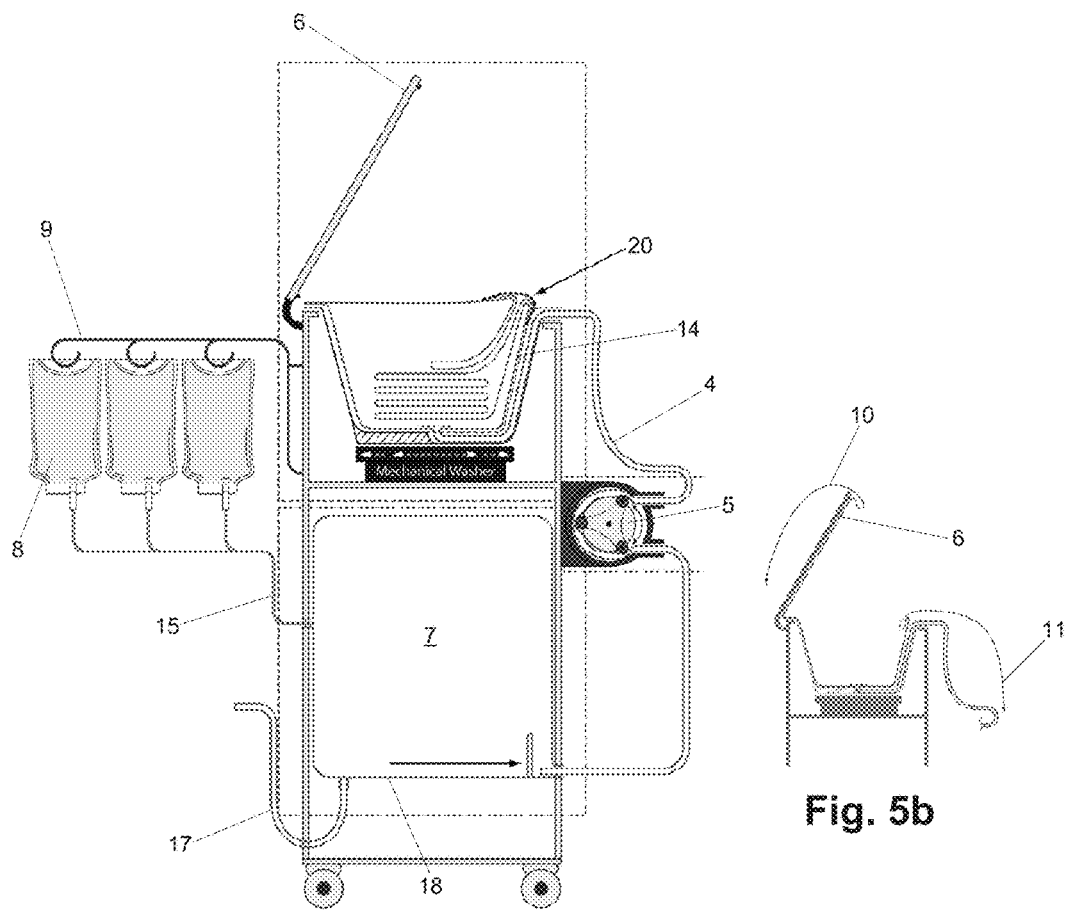
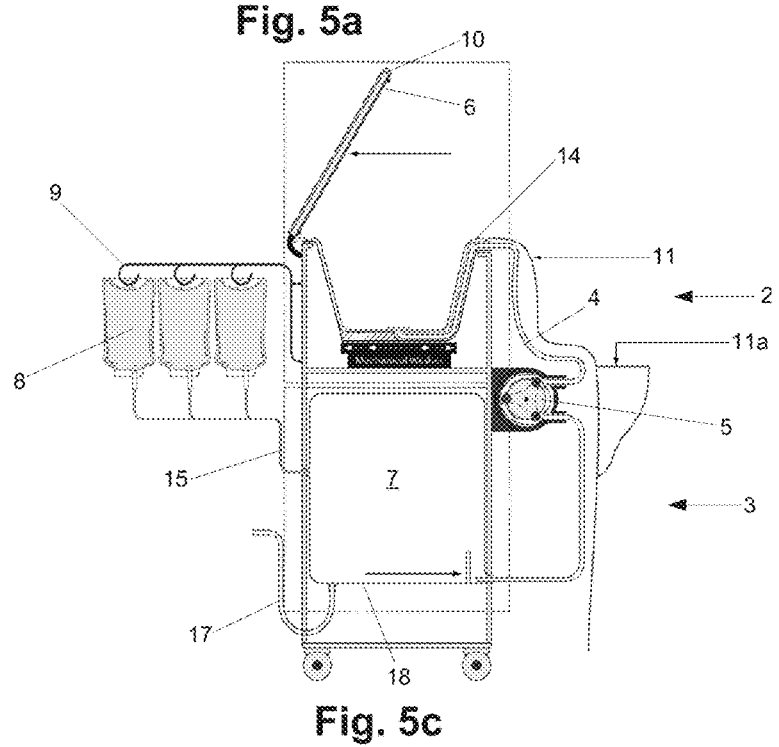
Fig. 5a
Fig. 5b
Fig. 5c

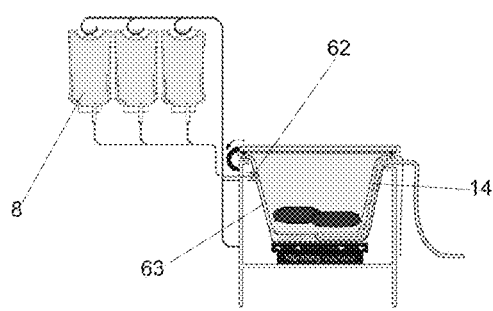
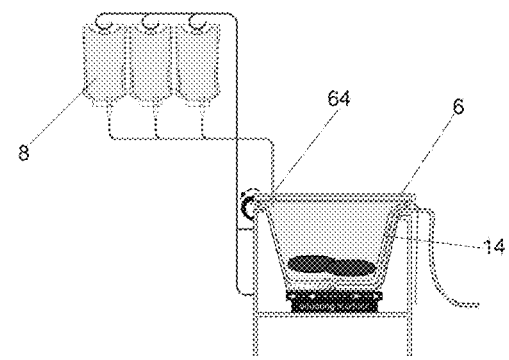
Fig. 9a        Fig. 9B
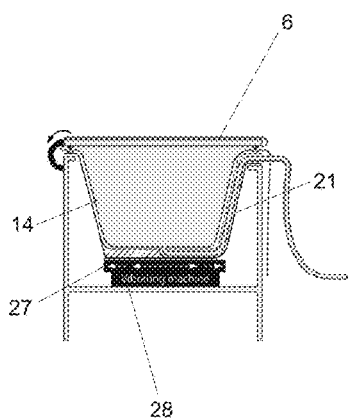
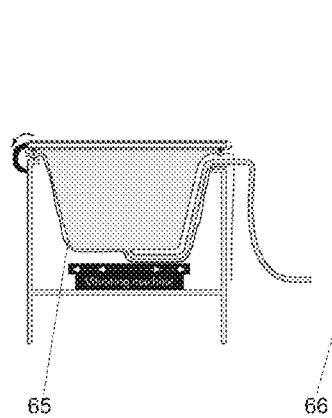
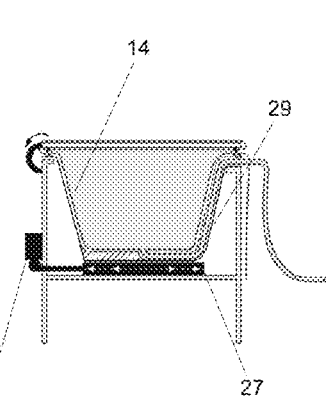
Fig. 10a        Fig. 10b        Fig. 10c

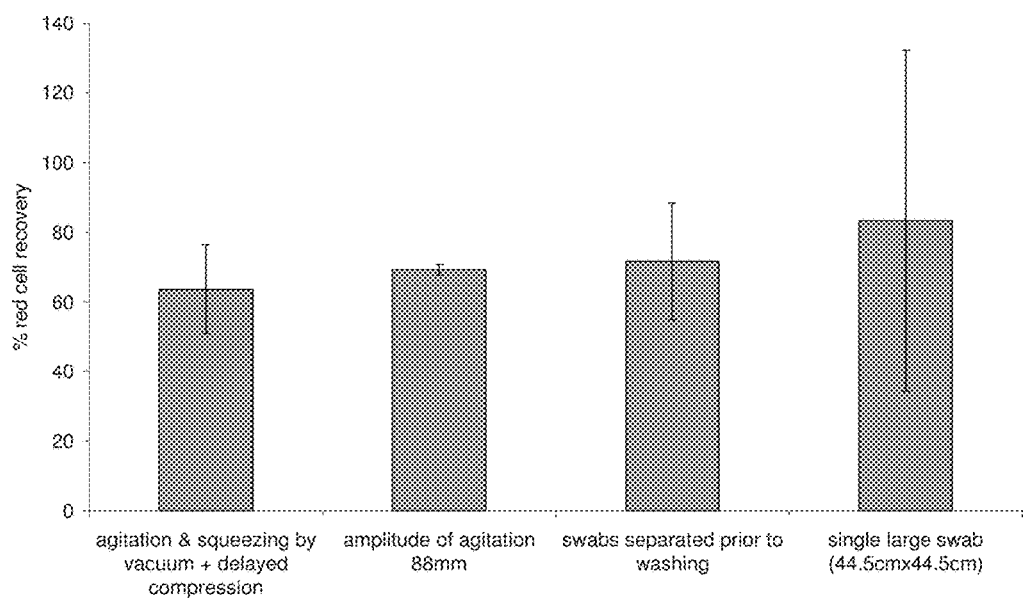
Fig. 31
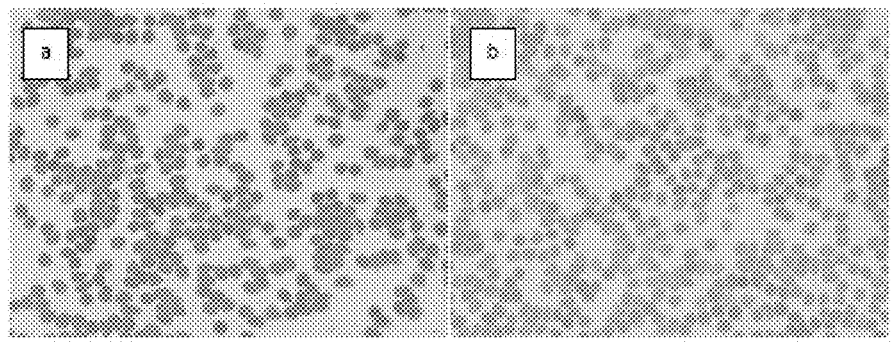
Fig. 32a
Fig. 32b

SURGICAL SWAB WASHING METHOD AND APPARATUS

CROSS REFERENCE TO RELATED APPLICATIONS

This application is a U.S. National Stage Application of International Application No. PCT/GB2013/052084 filed Aug. 5, 2013, which claims priority from United Kingdom Patent Application No. 1215097.5 filed Aug. 24, 2012. The entirety of all the above-listed applications are incorporated herein by reference.

The present invention relates to methods and apparatus for washing surgical swabs to extract viable red blood cells, particularly but not exclusively, for subsequent processing by cell salvage apparatus.

In many surgical procedures significant blood losses occur which can affect the outcome of the procedure and the patient's subsequent recovery. Historically, such blood loss has been replaced using donor blood transfusions either during or after the operation. Such allogeneic transfusions are expensive, depend on the availability of donor blood stocks and are associated with a number patient side effects and complications.

More recently, cell salvage technology has been developed which enables a patient's own blood to be recovered and recycled during an operation. This technique, known as intraoperative cell salvage (ICS), is now well adopted with a number of companies producing the required cell salvage machines and associated disposables. The UK National Health Service (NHS) currently uses approximately 2.1 million units of red blood cells per year of which 800,000 units are used to support surgical procedures at a cost of approximately £100 million. Over the last 5 years the adoption of ICS has reduced the use of donated blood in surgery by approximately 14% however the viability of cell salvage techniques is dependant on the ability of the surgical team to recover as much blood as possible from the surgical field, usually via a suction device connected to the cell salvage system. In many operations a substantial proportion of the overall blood loss is soaked up in surgical swabs and cannot be recovered by the cell salvage system. It has been estimated that blood loss to swabs is between 30% and 50% of the total blood loss during an operation.

It is possible to extract red blood cells from surgical swabs via a simple hand washing process in which the surgical swabs are soaked in sterile saline solution and then manually wrung out. The bloody saline is then directed to the cell salvage system. It has recently been demonstrated that implementation of this process within an operating theatre can increase overall red blood cell yields from the cell salvage system by up to 30%, potentially allowing valuable blood stocks to be conserved for life-threatening and emergency procedures.

Despite these clear benefits, hand washing of swabs is poorly adopted. Theatre staff are reluctant to handle blood soaked swabs as they pose a health and safety hazard, particularly if bone fragments are present which could puncture surgical gloves. Swab washing is a distraction to theatre staff whose primary role is to assist the surgeon, the process is messy and an open bowl of saline diluted blood within an operating theatre is an infection control risk and safety hazard. The hand washing process is inconsistent, is operator dependant and there is currently little understanding of the effect of the hand washing process on the subsequent viability of the recovered red blood cells.

An object of the present invention is to obviate or mitigate one or more of the aforementioned problems with current methods for washing surgical swabs.

According to a first aspect of the present invention there is provided a method for washing surgical swabs to extract viable red blood cells from said swabs, the method comprising: contacting at least one swab retaining viable red blood cells with saline-based wash solution in a receptacle under sterile conditions; and effecting automated compression and/or automated agitation of the receptacle containing the swab(s), saline-based wash solution and red blood cells to facilitate extraction of viable red blood cells from the swab(s) into the saline-based wash solution.

A second aspect of the present invention provides a surgical swab washing device comprising a receptacle for saline-based wash solution and at least one surgical swab retaining viable red blood cells, and an automated pump and/or automated agitator associated with said receptacle, said automated pump and/or automated agitator being operable to act on the receptacle once containing said saline-based wash solution and said swab(s) to facilitate extraction of viable red blood cells from the swab(s) into the saline-based wash solution.

The first and second aspects of the present invention provide means, for the first time, to effect the automated extraction of viable red blood cells from used surgical swabs. References herein to methods, processes and steps of such methods and processes as being "automated" shall be understood as characterising such methods, processes, steps etc as being effected by the use of a machine, device, apparatus etc to carryout the specified method, process or step and to distinguish automated methods, processes and steps from methods, processes and steps which are carried out manually, i.e. with human input. The definition of a method or process as being "automated" requires that at least one step in the method or process is automated and not that the entire sequence of steps defining the method or process is automated. The method and device affords a means of extracting viable red blood cells which no longer requires the manual agitation and/or compression of the swabs during washing. Instead, the swabs can now be subjected to optimised and repeatable agitation and/or compression conditions to achieve the desired level of cell extraction under sterile, aseptic conditions. The method and device of the first and second aspects of the present invention thus represent a significant advance in the field of intraoperative cell salvage which addresses many of the failings of the current manual method described above. The saline-based wash solution may be saline or may be a solution containing saline in combination with at least one further component, such as heparin.

While the receptacle may be rigid and non-compressable, it is preferred that the receptacle is flexible or compressable to facilitate automated compression of the receptacle containing the swab(s), saline-based wash solution and red blood cells by the extraction of fluid, such as saline-based wash solution or air, from within the receptacle. In this way, the volume of the contents of the receptacle can be decreased such that the flexible receptacle contracts against the swabs contained in the receptacle thereby applying a pressure to the swabs to compress them and remove any residual liquid. Compression of the receptacle in this way may be effected so as to apply a pressure of up to around 250 mmHg, preferably around 200 mmHg, to the swabs contained within the receptacle. Such pressures achieve satisfactory removal of bloody saline-based wash solution from the swabs without damaging the structure of the red blood cells extracted in the bloody saline-based wash solution.

The method may comprise automated compression of the flexible receptacle containing the swab(s), saline-based wash solution and red blood cells by the application of a physical force to at least one exterior surface of the receptacle. The physical force may be applied for around 1 to 10 minutes, more preferably around 5 minutes. The physical force may be generated by at least one driven member configured to contact said at least one exterior surface of the receptacle. In a first preferred embodiment said at least one driven member comprises a pneumatically driven plate positioned below the receptacle configured to be driven against said at least one exterior surface of the receptacle. In another preferred embodiment said at least one driven member comprises at least one roller configured to be driven over said at least one exterior surface of the receptacle. Optionally, said at least one driven member comprises a pair of rollers configured to be driven over opposed exterior surfaces of the receptacle, such as upper and lower exterior surfaces of the receptacle. In a further preferred embodiment the physical force is generated by increasing the pressure of a fluid within at least one sealed space located adjacent to the receptacle. Said at least one sealed space may be defined by a casing within which the receptacle is partially or fully received. The casing may receive the receptacle so as to define a first sealed space on a first side of the receptacle and a second sealed spaced on a second side of the receptacle. The first sealed space may be defined above the receptacle and the second sealed space may be defined below the receptacle. In a further preferred embodiment the sealed space may be defined by an expandable balloon.

Additionally or alternatively the method may comprise automated agitation of the receptacle containing the swab(s), saline-based wash solution and red blood cells by repeated application of a physical force to at least one exterior surface of the receptacle. Agitation may be applied to a rigid, non-compressable receptacle, or it may be applied to a flexible or compressable receptacle. The physical force may be generated by at least one driven member configured to repeatedly contact said at least one exterior surface of the receptacle. In one preferred embodiment said at least one driven member may comprise a pneumatically driven plate positioned below the receptacle, the plate configured to be repeatedly driven towards and away from said at least one exterior surface of the receptacle. The plate may be driven towards said at least one exterior surface of the receptacle once every 1 to 60 seconds, more preferably once every 1 to 30 seconds and most preferably once every 1 to 10 seconds. In another preferred embodiment said at least one driven member comprises an oscillating plate positioned so as to contact the receptacle, the plate configured to oscillate repeatedly while contacting said at least one exterior surface of the receptacle. The oscillating plate may oscillate through an orbit of length 1 to 5 mm, more preferably around 3 mm and/or may oscillate at a frequency of around 100 to 1000 rotations per minute, more preferably at a frequency of around 750 rotations per minute. In a further preferred embodiment said at least one driven member comprises at least one roller configured to be repeatedly driven over said at least one exterior surface of the receptacle. Said at least one driven member may comprise a pair of rollers configured to be repeatedly driven over opposed exterior surfaces of the receptacle, such as upper and lower exterior surfaces of the receptacle. In another preferred embodiment the physical force may be generated by increasing the pressure of a fluid within at least one sealed space located adjacent to the receptacle. Agitation of the receptacle may be effected by repeatedly increasing and decreasing the pressure of the fluid. Said at least one sealed space may be defined by a casing within which the receptacle is partially or fully received. The casing may receive the receptacle so as to define a first sealed space on a first side of the receptacle and a second sealed spaced on a second side of the receptacle. The first sealed space may be defined above the receptacle and the second sealed space may be defined below the receptacle. Alternatively, the sealed space may be defined by an expandable balloon.

Preferably the method comprises automated compression and automated agitation of the receptacle containing the swab(s), saline-based wash solution and red blood cells. Automated compression of the receptacle may be effected before, during and/or after automated agitation of the receptacle. It is preferred that automated agitation of the receptacle is effected before automated compression of the receptacle. It will be appreciated that in embodiments of the method where automated compression and automated agitation are both carried out, automated compression and automated agitation may each be achieved using any of the methods set out above. Conveniently, automated agitation is effected followed by automated compression by the extraction of bloody saline-based wash solution from the receptacle to a separate holding reservoir from where the bloody saline-based wash solution may then be pumped to a conventional cell salvage machine. In this way, removal of the bloody saline-based wash solution from the receptacle after agitation is achieved simultaneously with compression of the receptacle to squeeze out substantially all of the residual bloody saline-based wash solution retained by the swabs.

The saline-based wash solution containing swab(s) and red blood cells is preferably maintained at a temperature in a range of around 20 to 40° C., more preferably around 25 to 37° C. during compression and/or agitation. The device or apparatus of the present invention may incorporate any suitable means for controlling and/or maintaining the temperature of the saline-based wash solution at a desired level, such as a heater.

In the surgical swab washing device, the receptacle may be sealable and/or flexible. In the case where the receptacle is sealable, it is preferred that the automated pump and/or automated agitator is operable to act on the receptacle once the receptacle is sealed and containing saline-based wash solution and swabs. The automated pump may be operable to extract fluid, such as saline-based wash solution and/or air, from within the receptacle. Alternatively or additionally, the device may comprise at least one driven member configured to contact at least one exterior surface of the receptacle. In a preferred embodiment said at least one driven member may comprise a pneumatically driven plate positioned below the receptacle. In a further preferred embodiment said at least one driven member may comprise at least one roller, or a pair of rollers, a first roller disposed adjacent to a first exterior surface of the receptacle and a second roller disposed adjacent to a second exterior surface of the receptacle. By way of example, the first roller may be disposed above the first exterior surface, which is preferably an upper exterior surface of the receptacle, and the second roller may be disposed below the second exterior surface of the receptacle, which is preferably a lower exterior surface of the receptacle. In another preferred embodiment the device may comprise an automated compressor to pressurise a fluid received within at least one sealed space located adjacent to the receptacle. Said at least one sealed space may be defined by a casing for receipt of the receptacle or a part of the receptacle. The casing may be configured so as to define a first sealed space on a first side of the receptacle and a second sealed spaced on a second side of the receptacle. The first sealed space may be defined above the receptacle and the second sealed space may be defined below the receptacle. In a further preferred embodiment the sealed space is defined by an expandable balloon. A yet further preferred embodiment of the device comprises an oscillating plate positioned so as to contact the receptacle. The receptacle preferably incorporates a filter configured to allow the passage of saline-based wash solution and saline-based wash solution containing viable red blood cells through the filter but to prevent the passage of solid matter, such as bone shardes and the like.

A third aspect of the present invention provides apparatus for the extraction of viable red blood cells from surgical swabs retaining said cells, the apparatus comprising: a receptacle for at least one surgical swab retaining viable red blood cells; a source of saline-based wash solution in fluid communication with the receptacle; an automated pump and/or automated agitator associated with said receptacle, said automated pump and/or automated agitator being operable to act on the receptacle once containing said saline-based wash solution and said swab(s) to facilitate extraction of viable red blood cells from the swab(s) into the saline-based wash solution; a reservoir for saline-based wash solution containing viable red blood cells extracted from the swab(s); and at least one pump operable to pass saline-based wash solution from the source to the receptacle and/or to pass saline-based wash solution containing viable red blood cells extracted from the swab(s) to the reservoir.

A fourth aspect of the present invention provides a method for extracting viable red blood cells from surgical swabs retaining said cells, the method comprising: providing at least one surgical swab retaining viable red blood cells in a receptacle; providing saline-based wash solution in said receptacle so that it contacts said swab(s) such that viable red blood cells are extracted from the swab(s) into the saline-based wash solution; effecting automated compression and/or automated agitation of the receptacle containing the swab(s), saline-based wash solution and red blood cells to facilitate extraction of viable red blood cells from the swab(s) into the saline-based wash solution; and pumping saline-based wash solution containing viable red blood cells extracted from the swab(s) to a reservoir.

In the method according to the fourth aspect of the present invention the receptacle may be sealed after providing said at least one swab in the receptacle. Saline-based wash solution may be provided in the receptacle by pumping saline-based wash solution into the receptacle from a saline-based wash solution source via the reservoir. Sealing of the receptacle may be effected after providing the saline-based wash solution in the receptacle. The method may further comprise pumping saline-based wash solution containing viable red blood cells from the reservoir to cell salvage apparatus. The saline-based wash solution may be pumped from the reservoir to the receptacle and subsequently from the receptacle to the reservoir along the same conduit and/or using the same pump.

It will be appreciated that automated compression and/or automated agitation of the receptacle in the method according to the fourth aspect of the present invention may be achieved using any one or more of the features of the method according to the first aspect of the present invention by which automated compression and/or automated agitation of the receptacle is effected.

In the apparatus according to the third aspect of the present invention the receptacle is preferably flexible. The apparatus may further comprise a tube connecting the reservoir to the receptacle, said pump being operable to pump saline-based wash solution from the reservoir to the receptacle along said tube and subsequently from the receptacle to the reservoir along the same tube. Preferably a single continuous length of tubing connects the receptacle and the reservoir. While any suitable pump may be used, it is prefeable to use a peristaltic pump acting on the exterior of the tube so as to provide a relatively simple and robust means of maintaining the sterility of the surfaces of the components of the apparatus, e.g. the receptacle, reservoir and interconnecting tubing, during use of the apparatus. The automated pump may be operable to extract fluid, such as saline-based wash solution and/or air, from within the receptacle. The apparatus may comprise at least one driven member configured to contact at least one exterior surface of the receptacle to effect said automated compression and/or automated agitation of the receptacle. The apparatus may comprise an automated compressor to pressurise a fluid received within at least one sealed space located adjacent to said receptacle to effect automated compression and/or agitation of the receptacle. Moreover, the apparatus may comprise an oscillating plate positioned so as to contact said receptacle to effect agitation of the receptacle. It is preferred that automated agitation of the receptacle is effected, followed by automated compression of the receptacle by the extraction of bloody saline-based wash solution from the receptacle to the reservoir from where the bloody saline-based wash solution may then be transferred to a conventional cell salvage machine. In this way, removal of the bloody saline-based wash solution from the receptacle after agitation is achieved simultaneously with compression of the receptacle to squeeze out substantially all of the residual bloody saline-based wash solution retained by the swabs and to present the swabs in a compressed state suitable to be removed from the receptacle without the risk of leaking liquid over the user or the surrounding envirnnoment.

It will be appreciated that the automated pump and/or automated agitator of the apparatus according to the third aspect of the present invention may employ any one or more of the features of the automated pump and/or automated agitator of the device according to the first aspect of the present invention.

The receptacle may incorporate a first filter configured to allow the passage of saline-based wash solution and saline-based wash solution containing viable red blood cells through the first filter but to prevent the passage of solid matter, such as bone shardes and the like.

In a preferred embodiment of the reservoir forming part of the apparatus according to the third aspect of the present invention, the reservoir may incorporate a second filter configured to allow the passage of saline-based wash solution and saline-based wash solution containing viable red blood cells through the second filter but to prevent the passage of solid matter, such as bone shardes and the like. Where the receptacle is provided with a first filter, the second filter forming part of the reservoir may be omitted or vice versa, alternatively, both the receptacle and the reservoir may be provided with filters. The reservoir may define a lower region of smaller dimension, e.g. width and/or depth, than an upper region of the reservoir to focus the accumulation of red blood cells in said lower region. The lower region may be defined by at least one wall of the reservoir being inclined to the horizontal. An outlet may be defined by a wall of the reservoir which in part defines said lower region of the reservoir. The outlet may be connected to a tube linked to a cell salvage machine. In another preferred embodiment the reservoir may incorporate a filter configured to allow the passage of saline-based wash solution but to prevent the passage of viable red blood cells, within said reservoir said filter defining a first compartment for receipt of filtered saline-based wash solution having passed through said filter and a second compartment for receipt of viable red blood cells filtered from said saline-based wash solution. The second compartment is preferably in fluid communication with an outlet in a wall of the reservoir, which may be linked to a tube connected to a cell salvage machine.

Embodiments of the present invention will now be described, by way of example only, with reference to the accompanying drawings in which:

FIG. 5a is a schematic cross-sectional view of an alternative preferred embodiment of the apparatus shown in FIG. 1;

FIG. 5b is a detailed view of the upper section of the apparatus shown in FIG. 5a illustrating deployment of the protective drapes;

FIG. 5c shows the apparatus of FIG. 5a with the protective drapes deployed;

FIG. 7a illustrates the disposable components shown in FIG. 3;

FIG. 7b illustrates an alternative embodiment of the disposable components shown in FIG. 7a;

FIGS. 9a and 9b illustrate alternative preferred embodiments of the upper section of the apparatus of FIG. 6c employing different arrangements for the admission of saline into the surgical swab receptacle;

FIGS. 10a-10c illustrate alternative preferred embodiments of the upper section of the apparatus shown in FIG. 6a;

Figure 25:
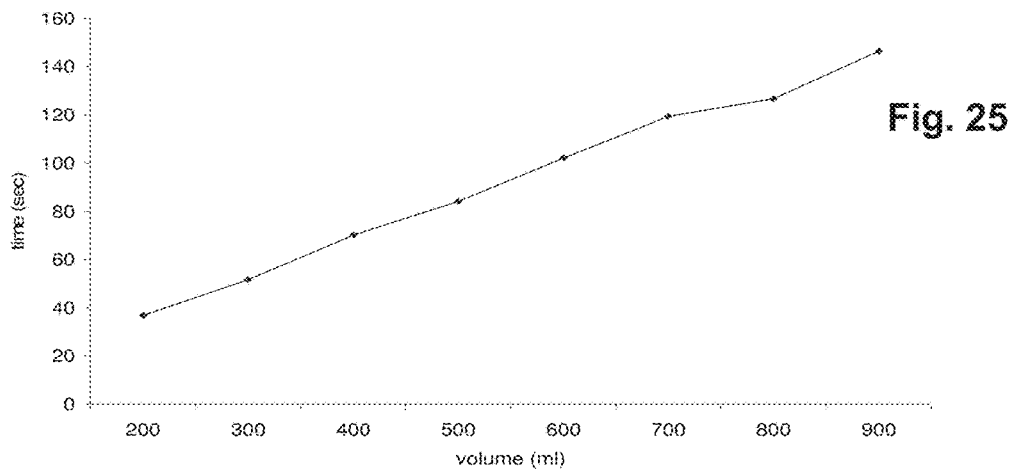
FIG. 25 is a graph illustrating the rate of fluid retrieval from swabs subjected to simultaneous squeezing under negative pressure and mechanical compression.
Figure 26:
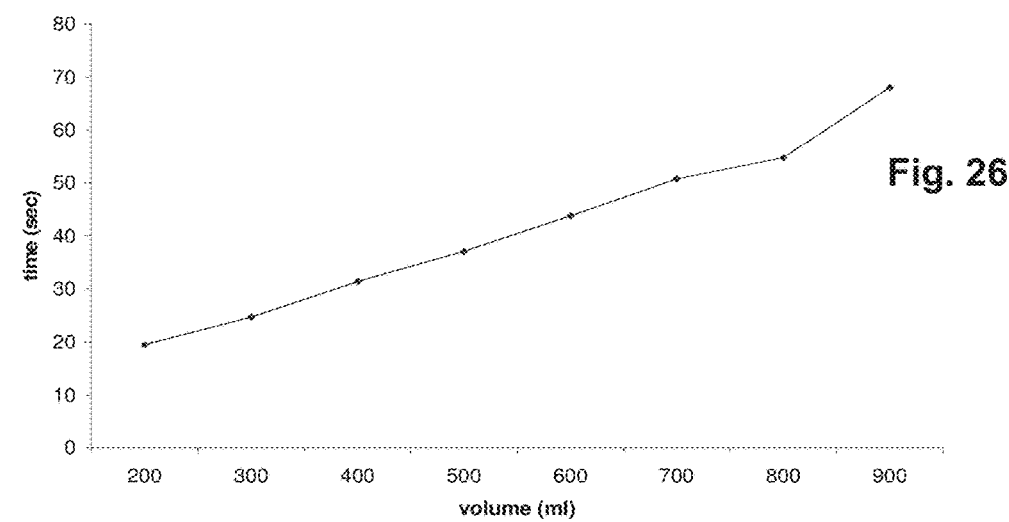
Figure 27:
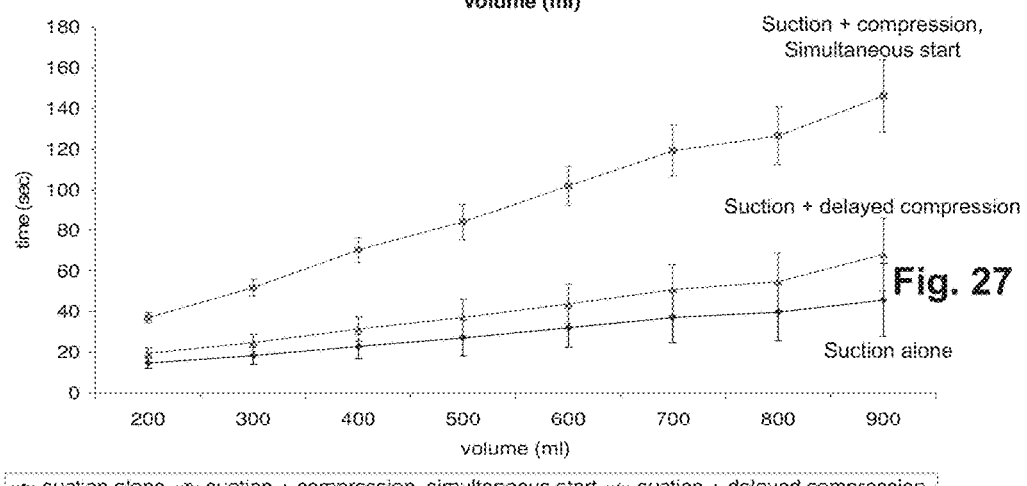
Figure 28:
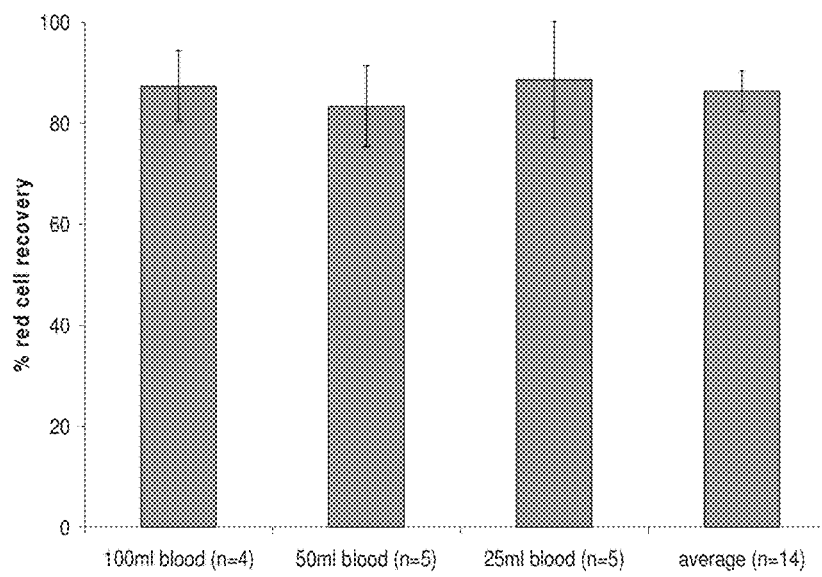
Figure 29:
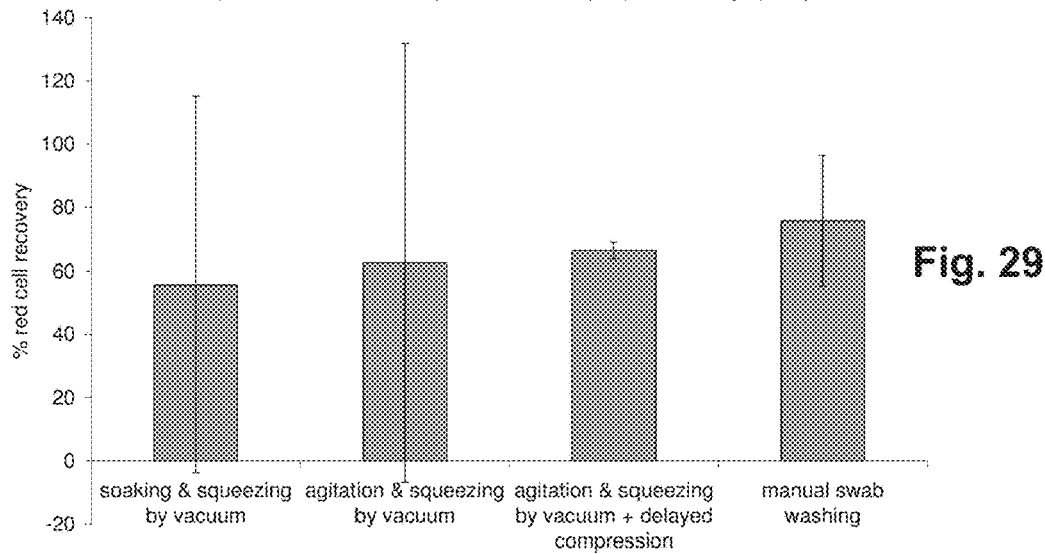
Figure 30:
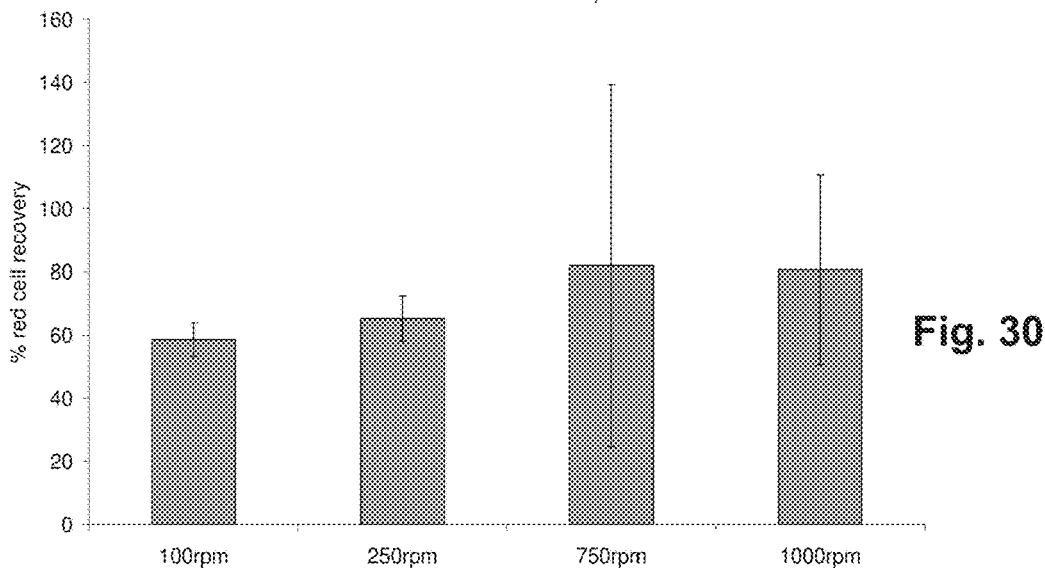

FIG. 26 corresponds to FIG. 25 but in the case where mechanical compression was delayed until after evacuation of fluid from a swab receptacle;

FIG. 27 is a comparison of evacuation rates for different methods of washing surgical swabs, all of which involve the application of negative pressure within the swab receptacle;

FIG. 28 is a bar chart illustrating the percentage of red cells recovered from saline solutions containing different concentrations of red blood cells using a conventional cell salvage machine;

FIG. 29 is a bar chart illustrating the percentage of recovered red cells using different automated methods of washing surgical swabs according to preferred embodiments of the present invention compared to the conventional method of manually washing such swabs;

FIG. 30 is a bar chart illustrating the results of a test to investigate the effect of changing the oscillation rate of an oscillating agitator on the rate of red cell recovery;

FIG. 31 is a bar chart illustrating the percentage of red cells recovered using a method employing (i) an increased agitation amplitude (employing a pneumatically driven plate), (ii) manually separating swabs before placing them in a swab receptacle, and (iii) a larger size swab; and FIGS. 32a and 32b are May Grunwald/Giesma stained blood films of samples of red blood cells (a) before swab washing and processing by conventional cell salvage techniques, and (b) after recovery from swabs washed in accordance with the present invention and processed using conventional cell salvage techniques.

Figure 1:
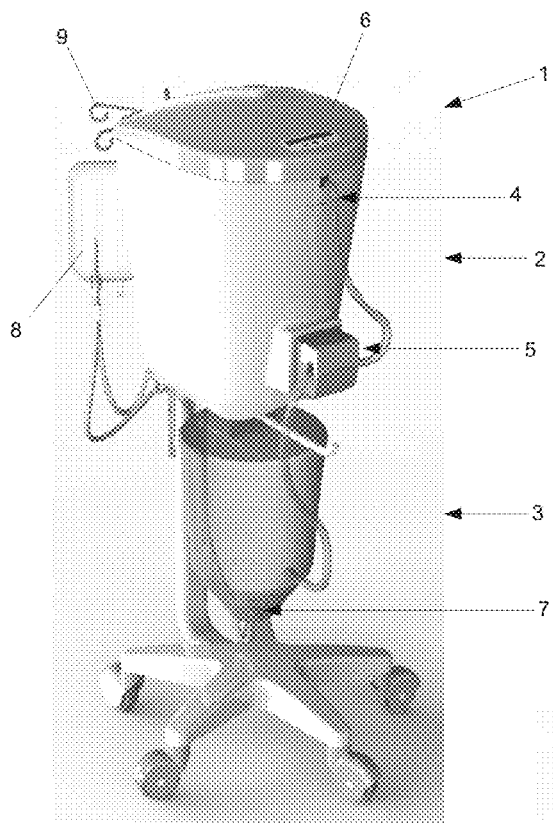
FIG. 1 is an illustration of apparatus according to preferred embodiments of the second and fourth aspects of the present invention.

Referring now to FIG. 1, there is shown an illustration of a preferred embodiment of apparatus 1 according to the third aspect of the present invention. The apparatus provides an automated means to extract viable red blood cells from used surgical swabs which can then be passed to a conventional cell salvage machine (not shown) for subsequent reintroduction to a patient during surgery.

The apparatus 1 includes an upper section 2 and a lower section 3 in fluid communication via a length of flexible tubing 4. Along the length of the tubing 4 at a position in between the upper 2 and lower 3 sections of the apparatus 1 is provided a peristaltic pump 5 which can be operated to pump fluid along the tubing 4 from the lower section 3 to the upper section 2 and in the reverse direction from the upper section 2 to the lower section 3. The upper section 2 comprises a hinged lid 6 which can be opened to allow used surgical swabs to be placed within a compartment defined by the upper section 2 of the apparatus 1 (shown in detail in later figures). The lower section 3 of the apparatus 1 comprises a fluid reservoir 7 which is in fluid communication with bags of saline 8 suspended from hangers 9 to the rear of the upper section 2 of the apparatus 1, as well as being in fluid communication via the tubing 4 to the upper section 2 of the apparatus 1.

Figure 2:
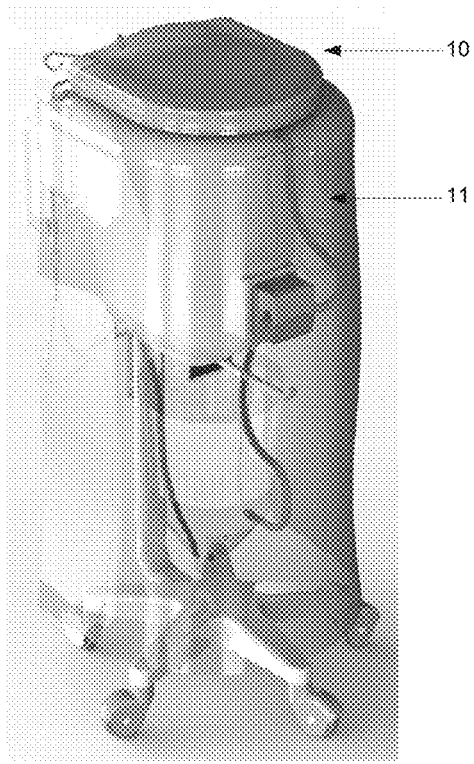
FIG. 2 is an illustration of the apparatus of FIG. 1 after deployment of protective drapes prior to use of the apparatus.

Referring now to FIG. 2, prior to use, upper and lower sterile protective drapes 10, 11 are drawn over the hinged lid 6 and the upper 2 and lower 3 sections of the apparatus 1. The protective drapes 10, 11 prevent blood or any other potential contaminants contacting the components of the upper 2 and lower 3 sections of the apparatus 1, and also allow the scrub nurse/assistant to operate the device without compromising asepsis.

Figure 3:
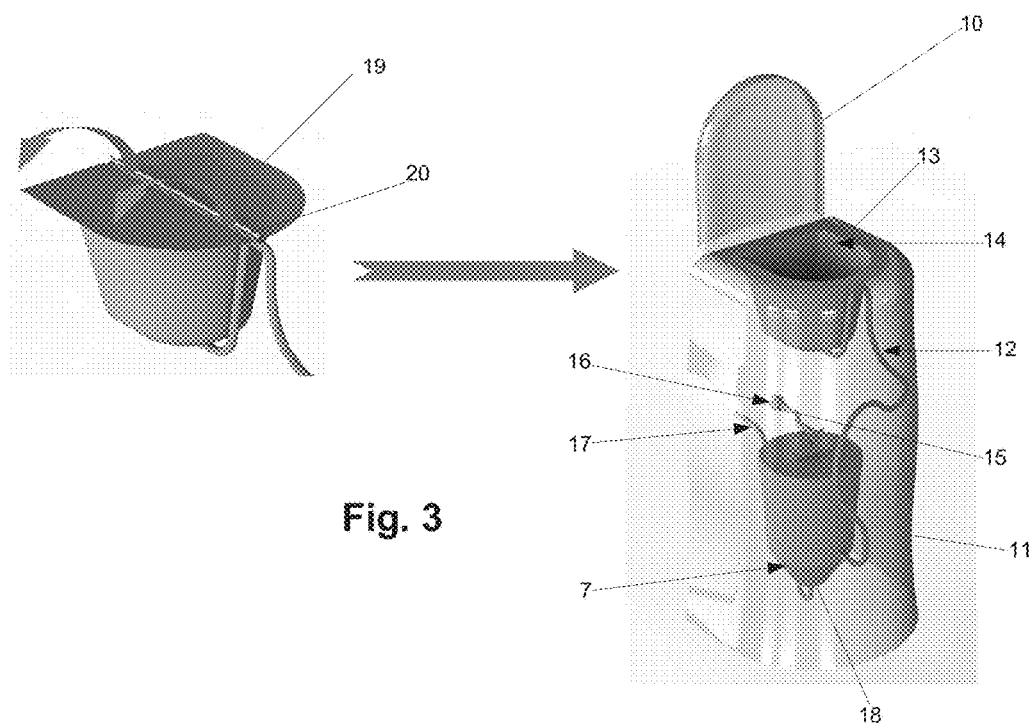
FIG. 3 is a modified version of the illustration of the apparatus in FIG. 2 in which only the protective drapes and a disposable component of the apparatus is shown (right hand side), and a detailed illustration of a surgical swab receptacle forming part of the disposable component prior to deployment of the protective drapes (left hand side)

The right hand image in FIG. 3 illustrates the arrangement of the protection drapes shown in FIG. 2 and a disposable subassembly 12 of the apparatus 1 shown in FIGS. 1 and 2 but with all other components of the apparatus 1 omitted for clarity. As can be seen in the right hand image in FIG. 3, an upper portion 13 of the disposable subassembly 12 comprises a flexible receptacle for used swabs in the form of a swab bag 14. The flexible tubing 4 connects to a port (not shown) defined by a bottom surface of the swab bag 14. Additionally, it can be seen that the fluid reservoir 7 in the lower section 3 of the apparatus 1 also forms part of the disposable subassembly 12, together with two tubes, a first tube 15 which includes a manifold 16, to connect the reservoir 7 to multiple bags of saline (not shown) and a second tube 17 connected to an aperture in a bottom surface 18 of the reservoir 7 through which saline containing extracted red blood cells can be pumped to a conventional cell salvage machine (not shown). As mentioned above, a limiting feature of conventional manual methods for washing used surgical swabs is that the bloody saline extracted from washed swabs can only be sent to the cell salvage machine when the cell salvage machine is not processing blood collected from the surgical field using the standard suction tubing, which is the time when the greatest quantity of viable red blood cells is being absorbed into the swabs, which might otherwise be salvaged. During heavy bleeds when the highest quantity of bloody swabs 14 is being produced, the reservoir 7 enables batches of bloody swabs 14 to be washed and the blood saline passed to the reservoir 7 where it can be held until such time as it can be pumped to the cell salvage machine. In this way, the reservoir 7 can act as a holding reservoir for bloody saline during heavy bleeds, thereby greatly increasing the proportion of viable red blood cells that can be salvaged during a surgical procedure. Additionally, incorporation of the reservoir 7 into the apparatus 1 enables saline to be re-used during the swab washing procedure so that, for example, 10 to 20 standard size swabs can be processed using the same standard volume of saline, thus reducing the volumes of saline sent to the cell salvage machine.

The left hand image in FIG. 3 provides a more detailed view of the swab bag 14 before deployment of the protective drapes 10, 11. The swab bag 14 would be provided in a sterilised outer protective covering (not shown) during transportation, handling and storage. The swab bag 14 shown in the left hand image in FIG. 3 has been removed from its protective covering immediately prior to use. As can be seen, the swab bag 14 is initially closed by an overlying protective lid 19 having a central opening which is initially sealed with a tear-off strip 20. Removal of the tear-off strip 20 allows the lid 19 to be opened and the upper and lower protective drapes 10, 11 withdrawn from inside the swab bag 14 and located over the lid 6 and upper 2 and lower 3 sections of the apparatus 1. Although not shown in FIG. 3, tear-off plugs are provided on the open ends of all tubes and manifolds that form part of the disposable subassembly 12. This ensures that the sterile interior surface of these tubes will not be exposed to the atmosphere until the disposable subassembly is ready to be connected to the bags saline of saline 8 and/or the cell salvage machine (not shown).

By enclosing the sterile protective drapes 10, 11 inside the swab bag 14 and by using the peristaltic pump 5, the disposable subassembly 12 can be provided as a single-piece element that can be inserted into the apparatus 1 by operators who are not sterile and who are outside of the sterile field in which the apparatus is going to be used. As a result, the apparatus 1 can be set-up ready for use at any convenient time and does not have to be set-up within the sterile field immediately before use. Once the disposable subassembly 12 has been loaded into the apparatus 1, all that is required in order to use the apparatus 1 is to provide it in the sterile field and for a practitioner who has undergone a surgical scrub procedure and is deemed 'sterile' to remove the tear-off strip 20 and then locate the sterile protective drapes 10, 11 over the upper 2 and lower 3 sections of the apparatus 1. This innovative design affords a number of advantages. For example, it allows the apparatus 1 to be quickly brought into use during operations where cell salvage was not originally planned but where a significant bleed has occurred resulting in the generation of bloody swabs. The use of the peristaltic pump 5 as opposed to other designs of pump, e.g. a centrifugal pump, also offers advantages in relation to sterility and set-up of the apparatus. While a centifugal pump or the like may be used, this would necessitate sterilising the inside of the pump between each use and require the tubing to be provided in at least two sections, a first section connecting the pump to the swab bag 14 and a second section connecting the pump to the fluid reservoir 7. It will be appreciated that each section of the tubing would then probably have to be connected to the centrifugal pump within the sterile field and any pump connectors and associated components would have to be sterilised. By way of a further alternative pump arrangement, the disposable sub-assembly 12 may incorporate one or more disposble pump heads, e.g. a rotary vane pump, for direct connection to a suitable motor. Such an arrangement may supplement or replace the peristaltic pump 5.

Figure 4:
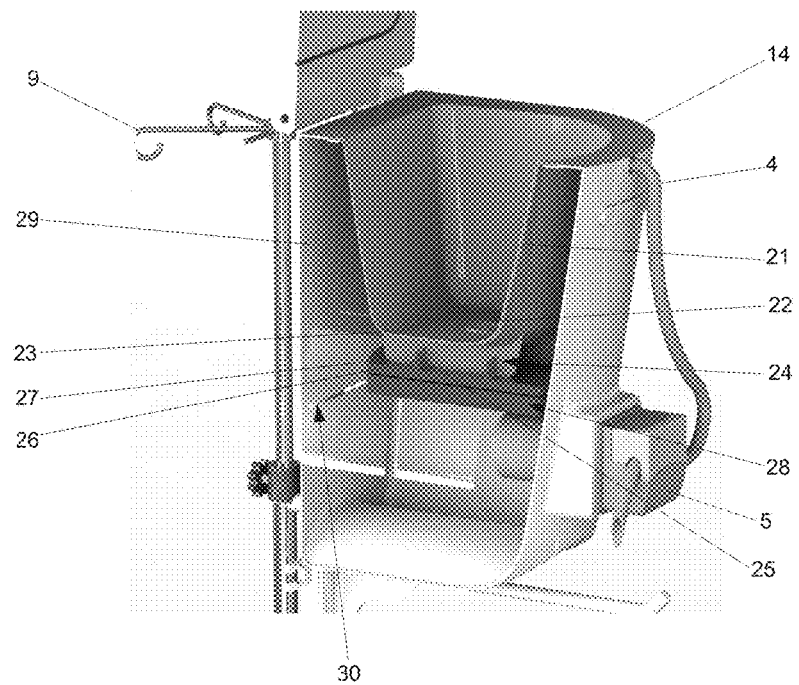
FIG. 4 is a part sectioned view of an upper section of the apparatus of FIG. 1.

FIG. 4 is a part-cut-away illustration of the upper section 2 of the apparatus 1. As can be seen, the flexible swab bag 14 is supported within a complementary shaped rigid container 21. A port 22 is defined by a lower surface 23 of the swab bag 14, which is connected to the flexible tubing 4. The port 22 may be provided with a filter to prevent unwanted matter, such as large pieces of debris, bone fragments, and the like from swabs entering the tubing 4. Provision of this filter may negate the need to provide a filter in the fluid reservoir 7 (described below), however, it will be appreciated that it may be desirable to incorporate a filter in the port 22 in the upper section 2 of the apparatus 1 as well as a filter in the fluid reservoir 7 in the lower section 3 of the apparatus. A bottom wall of the rigid container 21 defines a channel (not shown) for receipt of the tubing 4 as it extends from the port 22 to a side of the rigid container 21. The bottom wall of the rigid container 21 also defines two downwardly extending flanges 24 (only one of which is visible), each of which defines a pair of upwardly extending slots 25 for receipt of complementary projections 26 defined by an upper plate 27 of an agitator. The agitator also includes a lower plate 28 to support the upper plate 27 during displacement of the upper plate 27, which in turn displaces the rigid container 21 supporting the swab bag 14. An outer casing 29 of the upper section 2 of the apparatus 1 defines one or more vents 30 to enable atmospheric air to pass freely into and out of the outer casing 29 to facilitate effective evacuation of the swab bag 14 when placed under vacuum, as described in relation to subsequent figures. The rigid container 21 is located directly underneath the flexible swab bag 14 so as to contain any swabs or liquids that spill from the swab bag 14 in the event that the swab bag 14 ruptures during use. In this way, the components underneath the swab bag 14, in particular the various components of the agitator, are protected from contamination. The rigid container 21 is removeably supported by the outer casing 29 such that, should a spill occur, the swab bag 14 and the rigid container 21 can be simply removed from the outer casing, the swab bag 14 discarded, the rigid container 21 cleaned and placed back into the outer casing 29 and a new swab bag 14 located within the rigid container 21. The volume of the rigid container 21 is sufficiently large to contain all of the liquids and swabs that may be used during a washing cycle, thereby ensuring that nothing can escape from the rigid container 21 that might represent a contamination risk.

A more detailed illustration of the various components of the apparatus 1 and the method for deploying the protective drapes 10, 11 is illustrated in FIGS. 5a to 5c. With reference to FIG. 5a, the swab bag 14 is shown in its initial sealed state with the tear-off strip 20 in place. When it is desired to use the apparatus 1, the tear-off strip 20 is removed and the previously folded upper and lower protective drapes 10, 11 placed over the lid 6 and over the upper section 2 of the apparatus 1 as shown in FIG. 5b. The upper protective drape 10 is then secured over the lid 6 and the lower protective drape 11 drawn down over the lower section 3 of the apparatus as shown in FIG. 5c. FIG. 5c also illustrates a swab holding bag 11a formed as part of the lower drape 11. This is provided to enable users to store swabs in a sterile environment before placing them into the swab bag 14. This may be required, for example, during heavy bleeds when the quantity of bloody swabs exceeds the capacity of the swab bag 14. The swab holding bag 11a may be substituted or supplemented with alternative designs of swab holding areas, such as a shelf forming part of the apparatus 1, which may for example fold out from the apparatus 1 or be moulded so as to form an integral part of the apparatus 1. Once the protective drapes 10, 11 are in place, the apparatus may then be used as now described with reference to FIGS. 6a to 6g.

Figures 6A, 6B, 6C:
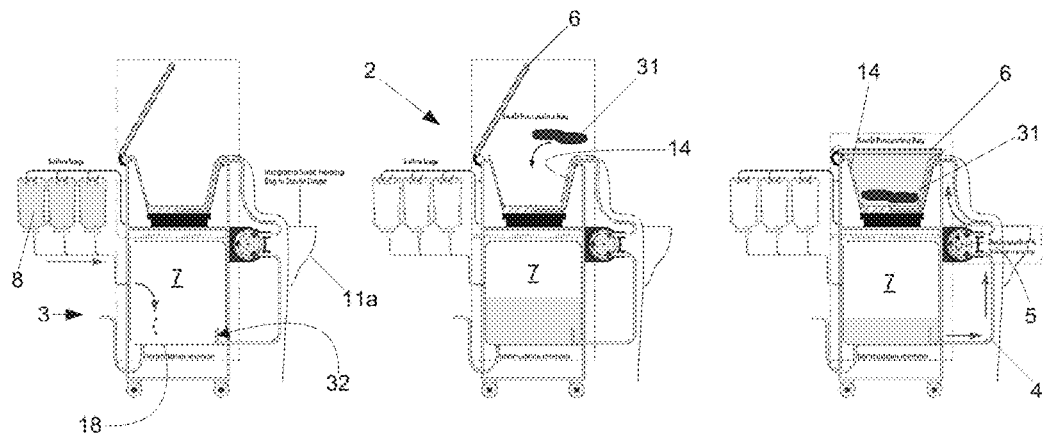
FIGS. 6a-6g illustrate steps in the method of using the apparatus of FIG. 5c to wash surgical swabs to extract viable red cells there from for subsequent transmission to a cell salvage machine.

The first step in using the apparatus 1 is shown in FIG. 6a where saline is pumped from a plurality of saline bags 8 through an aperture in an upper section of the fluid reservoir 7 in the lower section 3 of the apparatus 1. Once the desired volume of saline has been dispensed into the fluid reservoir 7, used swabs 31 retaining red blood cells can then be placed in the swab bag 14 supported in the upper section 2 of the apparatus 1 as shown in FIG. 6b. Once an appropriate number of swabs 31 has been placed into the swab bag 14, the lid 6 is closed and sealed shut. Saline from the fluid reservoir 7 is then pumped using a peristaltic pump 5 up the flexible tubing 4 in the direction of the arrows shown, from the fluid reservoir 7 and into the swab bag 14 to contact the used swabs 31 as shown in FIG. 6c. The swab bag 14 may be provided with a gas outlet (not shown) to enable gas within the swab bag 14 to escape during the introduction of saline into the swab bag 14.

Figures 6D, 6E:
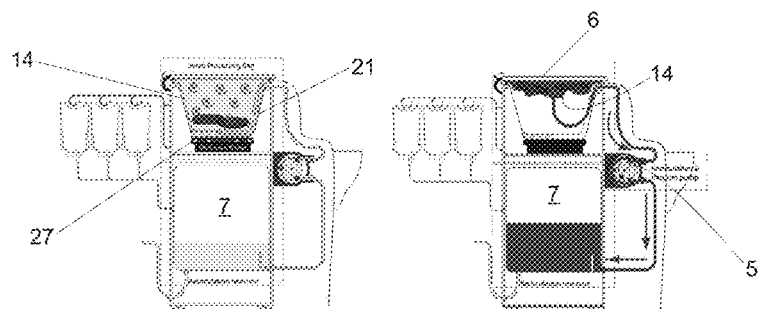

Once the desired volume of saline has been dispensed into the swab bag 14, the swab washing process is then initiated by activation of the agitator to oscillate the upper plate 27 of the agitator, which in turn agitates the rigid container 21 within which the swab bag 14 is supported as shown in FIG. 6d. Agitation of the rigid container 21 agitates the contents of the swab bag 14 and encourages the extraction of red blood cells from the used swabs 31 into the saline in which the swabs 31 are submerged.

After an appropriate period of time, as shown in FIG. 6e, the peristaltic pump 5 is operated in the reverse direction to pump the saline now containing red blood cells from the swab bag 14 back down to the fluid reservoir 7 in the lower section 3 of the apparatus 1 in the direction of the arrows shown. The lower reservoir 7 defines a baffle 32 upstanding from the lower wall 18 of the fluid reservoir 7 adjacent to an end of the tubing 4 through which bloody saline is pumped into the fluid reservoir 7. The purpose of the baffle 32 is to prevent aeration of the bloody saline as it enters the fluid reservoir 7. Removal of the bloody saline from the swab bag 14 creates a negative pressure within the bag 14 such that atmospheric pressure surrounding the swab bag 14 causes the swab bag 14 to compress against the swabs 31 retained in the bag 14 which are eventually forced against the lid 6 of the apparatus 1. Provided a great enough negative pressure is applied, this method produces a ball of moist swabs 31 at the top of the swab bag 14, which can be easily retrieved and from which there is essentially no risk of liquids dripping. Another advantage of this method is that it can be applied to essentially any number or volume of swabs 31 without having to adjust any operational parameters or mechanical settings. It also ensures that the pressure applied to the swabs 31 is applied uniformly and limited by the evacuation pressure applied. It will be appreciated that if the pressure on the swab bag 14 is applied using a hard surface the contact pressure is dependant on the shape taken up by the swabs 31 and the contact area between the hard surface and the swabs 31. This may result in swabs 31 in some areas of the swab bag 14 experiencing a very high contact force, which risks damaging the structure of the red blood cells contained within the swabs 31. Application of a negative pressure is also a relatively gentle process that enables the applied pressure to be slowly increased at any desired rate. Typically, the swabs 31 are not subjected to higher pressures until the majority of the bloodly saline has been sucked out of the swab bag 14 when higher vacuum pressures are established within the swab bag 14. This represents another significant advantage of this method since it ensures that the majority of the red blood cells experience only relatively gentle pressures during the evacuation process, thereby minimising or avoiding cell damage.

Figures 6F, 6G:
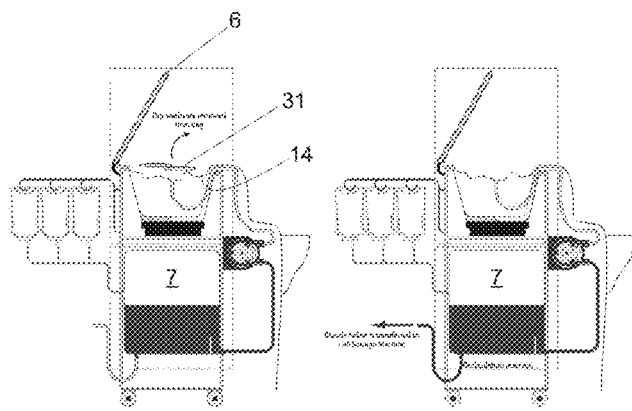

Once a batch of blood swabs has been washed the peristaltic pump is turned off and, as shown in FIG. 6*f*, the lid 6 opened to enable removal of the now dried swabs 31 for subsequent disposal.

The above-described washing cycle can then be repeated any desirable number of times, reusing the bloody saline within one surgical operation, to wash a number of batches of swabs.

Finally, as shown in FIG. 6*g*, the bloody saline from the fluid reservoir 7 is pumped to a conventional cell salvage machine (as shown) from where recovered cells can be recycled back to a patient undergoing a procedure.

When it is desired to use the apparatus 1 again, all that is required is to remove the drapes 10, 11 and the disposable subassembly 12 from the apparatus 1 and then suspend a new disposable assembly 12 and a new source of saline from the apparatus 1.

It will be appreciated that the process described above with reference to FIGS. 6*a* to 6*g* provides a non-contact, automated process for washing used surgical swabs to extract viable red blood cells there from for subsequent processing by a conventional cell salvage machine. In this way, the problems mentioned above in relation to conventional manual methods of washing surgical swabs are addressed in a manner which enables at least the same, if not greater, quantities of viable red blood cells to be extracted from used surgical swabs as compared to the conventional manual swab washing method.

Figures 7A, 7B:
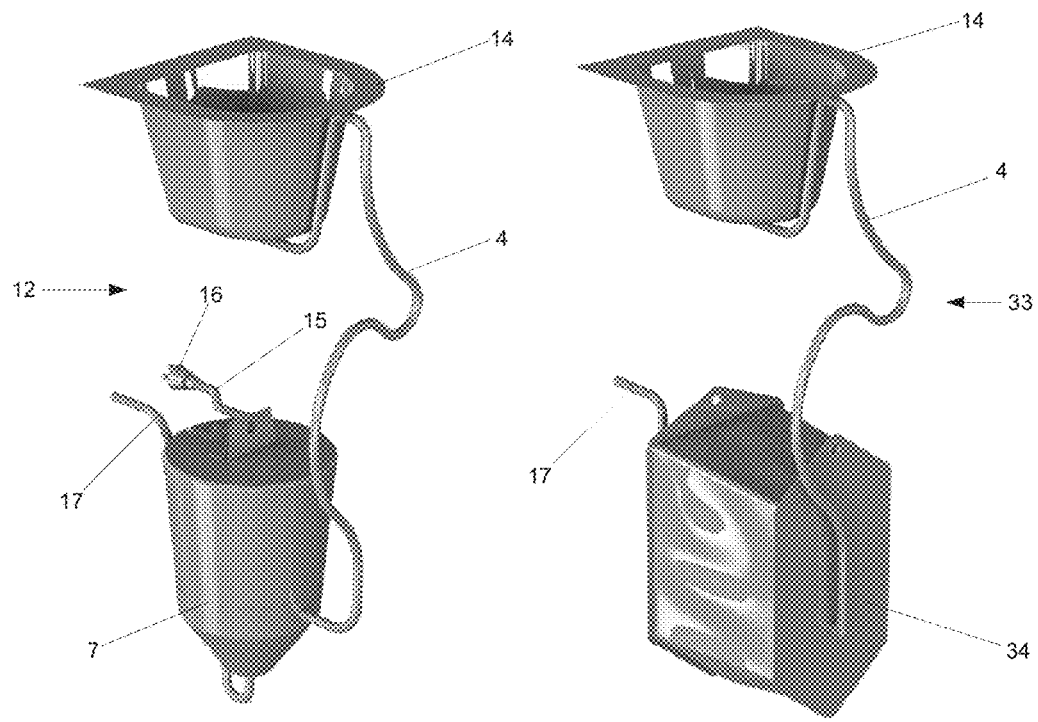

It will be appreciated that numerous modifications can be made to the apparatus 1 shown in FIGS. 1 to 6*g* while still remaining within the scope of the present invention defined in the claims. For example, as shown in FIG. 7, the disposable subassembly 12 depicted in the right hand image of FIG. 3 and shown again in isolation in FIG. 7*a* may be substituted with a disposable subassembly 33 incorporating a fluid reservoir 34 of different shape, such as that shown in FIG. 7*b*. Moreover, while not depicted in FIG. 7*b*, it will be appreciated that the specific size and/or shape of the flexible swab bag 14 may also vary from that shown in FIGS. 1 to 6*g*. Furthermore, while the disposable subassemblies 12, 33 shown in FIGS. 7*a* and 7*b* are each illustrated as unified components it will be appreciated that any one or more components of each subassembly 12, 33 may be manufactured separately and then connected together prior to use of the apparatus 1. For example, the swab bag 14 and the fluid reservoir 7, 34 may be formed as separate components, which are themselves separate to the flexible tubing 4 which connects the swab bag 14 to the fluid reservoir 7, 34 and the tubing 15, 17 which connects the lower reservoir 7, 34 to the source of saline and the cell salvage machine (not shown).

It will also be noted that the alternative embodiment of the fluid reservoir 34 shown in FIG. 7*b* is not connected to tubing 15 for connection via the manifold 16 to a source of saline. This is because the disposable subassembly 33 is designed for use with alternative means for supplying saline to the swab bag 14, such as those embodiments described below in relation to FIGS. 9*a* and 9*b*.

Figures 8A, 8B, 8C:
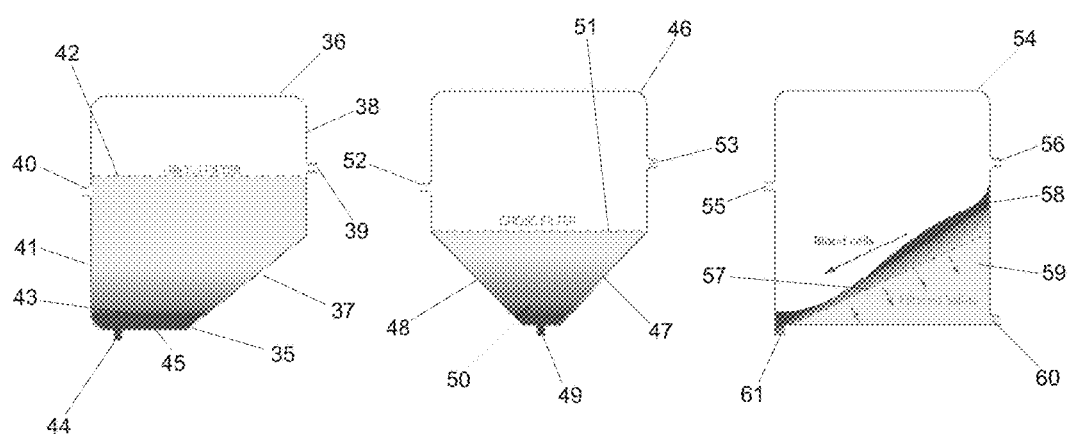
FIGS. 8a-8c are schematic illustrations of three different embodiments of a reservoir for saline and extracted red blood cells that can be provided in a lower section of the apparatus of FIG. 1.

FIGS. 8*a* to 8*c* show further preferred embodiments of the fluid reservoir in schematic cross-section. FIG. 8*a* illustrates an arrangement in which a lower surface 35 of a fluid reservoir 36 defines a ramped section 37 from a side 38 of the reservoir 36 through which bloody saline is admitted through a port 39 back into the fluid reservoir 36. A saline port 40 is defined on an opposite wall 41 of the fluid reservoir 36 with a gross filter 42 extending across a width of the reservoir 36 in between the saline port 40 and the port 39 through which bloody saline is admitted back into the fluid reservoir 36. In this way, saline can be pumped from the fluid reservoir 36 out of the port 39 above the gross filter 42 for introduction into the swab bag 14 but any foreign bodies over a particular size cannot pass through the gross filter 42 when the bloody saline is pumped back into the fluid reservoir 36. As bloody saline is pumped back into the fluid reservoir 36 the red blood cells will accumulate in a lowermost region 43 of the fluid reservoir 36 towards the bottom of the ramped section 37. A further port 44 is provided in a bottom section 45 of this lowermost region 43 to enable the accumulating red blood cells to be pumped to a cell salvage machine. It will be appreciated that the provision of the gross filter 42 represents a preferred feature of the fluid reservoir 7, however, the gross filter 42 may be omitted if a filter is already provided in the port 22 or orifice in the upper section 2 of the apparatus 1.

FIG. 8*b* illustrates an alternative embodiment to that shown in FIG. 8*a* in which a fluid reservoir 46 defines two ramped surfaces 47, 48 which focus red blood cells towards a port 49 in a lowermost region 50 of the fluid reservoir 46 from which accumulating red blood cells can be pumped to a cell salvage machine. Ramped surfaces 47, 48 may be replaced with a conical-shaped lower section of the fluid reservoir 46 if desired. A gross filter 51 extends across a width of the fluid reservoir 46 but is located vertically below both a saline port 52 and a port 53 through which bloody saline is pumped back into the fluid reservoir 40. Gross filter 51 may be omitted if a filter is already provided in the port 22 or orifice in the upper section 2 of the apparatus 1.

In FIG. 8*c* there is shown a further alternative embodiment of a fluid reservoir 54 in which a saline port 55 and port 56 through which bloody saline is pumped back into the fluid reservoir 54 are essentially the same as in the embodiment shown in FIGS. 8*a* and 8*b* but now a fine filter 57 extends at an angle to the horizontal such that it is now inclined so as to define an upper region 58 against which red blood cells can accumulate whilst allowing saline to filter through to accumulate within a lower region 59 of the fluid reservoir 54 from where it can be pumped out via a port 60. A further port 61 through which extracted red blood cells can be pumped back to a cell salvage machine is defined at a lowermost point of the fluid reservoir 54 where the lowermost point of the ramped fine filter 57 meets a lowermost wall 45 of the fluid reservoir 54.

By way of further example, FIGS. 9*a* and 9*b* illustrate alternative arrangements for feeding saline into the swab bag 14. In the arrangement shown in FIG. 9*a*, rather than pumping saline through a fluid reservoir, it is admitted directly into the swab bag 14 via a port 62 defined in a side wall 63 of the rigid container 21 which supports the swab bag 14. In the FIG. 9*b* embodiment, a port 64 is defined in the hinged lid 6 in the upper section 2 of the apparatus 1. In the arrangements shown in FIGS. 9*a* and 9*b* the saline may be admitted into the swab bag 14 under gravity rather than requiring a pump. It will be appreciated, however, that a pump may be used if desired.

As a yet further example, FIGS. 10a to 10c illustrate alternative arrangements of a rigid container to support swab bags 14 and an agitator. In FIG. 10a the arrangement is essentially as shown in FIGS. 4 to 6g. In the arrangement shown in FIG. 10b, the rigid container 21 of FIG. 10a is replaced with a flexible outer containerb 65. In the FIG. 10c embodiment the actuator 66 for the upper oscillating plate 27 is located outside the outer casing 29 of the upper section 2 of the apparatus 1. In this way, the agitator 66 mechanism is protected from being contacted by any fluid from the swab bag 14 which inadvertently enters the outer casing 29 of the upper section 2 of the apparatus 1.

FIGS. 11a to 11f schematically illustrate different means for facilitating the extraction of viable red blood cells from used surgical swabs.

Figure 11A:
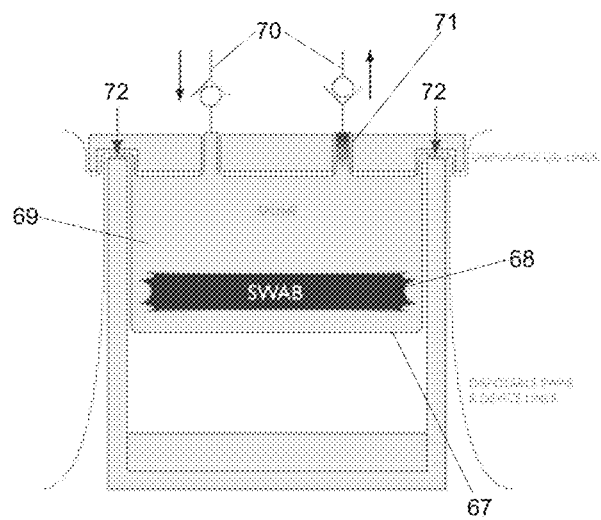
FIG. 11a is a schematic illustration of a first embodiment of a surgical swab washing device according to the second aspect of the present invention which may be employed in apparatus according to the third aspect of the present invention.

In the first embodiment shown in FIG. 11a, the swab bag 67 containing used swabs 68 and saline 69 is not subjected to agitation. Instead, the used swabs 68 are soaked for an appropriate period of time in the saline 69 before actuation of a vacuum pump 70 to withdrawn saline containing viable red blood cells 71 from within the swab bag 67. In this way, the swabs 68 and saline 69 within the swab bag 67 are subjected to compression under negative pressure to encourage the extraction of viable red blood cells from the swabs 68. This arrangement is advantageous since it provides an aseptic means of washing the swabs 68. It is easy to use and affords a non-contact, automated method of washing swabs to extract viable red blood cells there from. If there is a risk that the swabs 68 may contain foreign bodies, it will be desirable to manufacture the swab bag 67 from a material which will be resistant to puncture by such foreign bodies. It will also clearly be important to provide effective seals 72 at the top of the swab bag 67 to ensure an effective negative pressure can be applied to the contents of the swab bag 67.

Figure 11B:
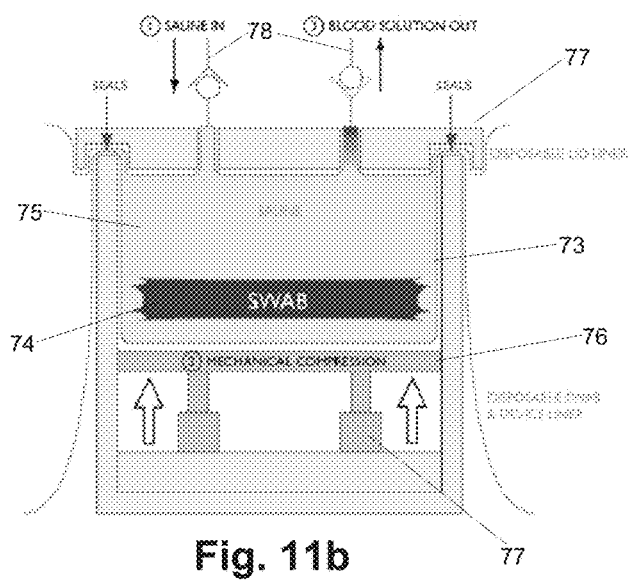
FIG. 11b is a schematic illustration of a second embodiment of a surgical swab washing device according to the second aspect of the present invention which may be employed in apparatus according to the third aspect of the present invention.

In FIG. 11b there is shown an alternative embodiment in which a swab bag 73 containing used swabs 74 and saline 75 is agitated to encourage viable red blood cells to pass from the swabs 74 into the saline 75. The means of agitation in this embodiment is a horizontal plate 76 mounted below the swab bag 73 and supported on pneumatic actuators 77 which drive the plate 76 up and down against the swab bag 73. Such a mechanism enables different levels of pressure to be applied by the plate 76 to the swab bag 73, different amplitudes of agitation to be employed and also different frequencies of agitation. This design therefore provides a relatively simple, yet robust, means of applying an optimal means of agitation to the used swabs 74 to maximise the extraction of viable red blood cells into the saline 75.

Moreover, once the plate 76 has been used to agitate the swab bag 73, its range of motion can then be extended so as to force the contents of the swab bag 73 against a lid 77 thereby maximising compression of the swabs 74 with the intention of maximising the extraction of red blood cells from the swabs 74. A pump 78 is provided to apply a negative pressure to the contents of the swab bag 73 after agitation but before final compression of the swab bag 73 in a similar manner described in relation to FIG. 11a.

Figure 11C:
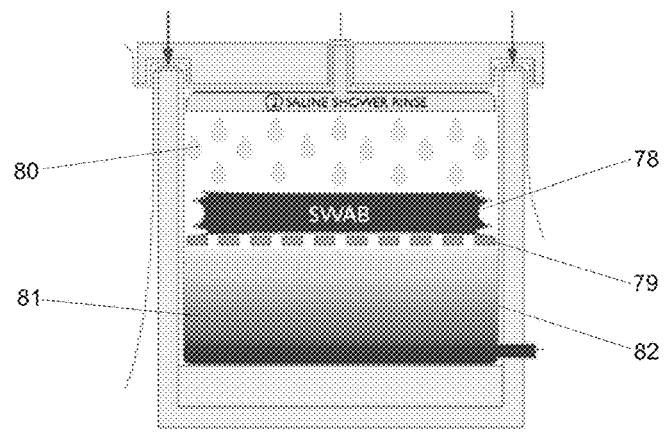
FIG. 11c is a schematic illustration of a third embodiment of a surgical swab washing device according to the second aspect of the present invention which may be employed in apparatus according to the third aspect of the present invention.

In FIG. 11c there is shown a further embodiment in which used swabs 78 are supported on a filter 79 and saline 80 is applied to the swabs 78 from a plurality of apertures so as to provide a showering effect. As the saline 80 is dripped onto the swabs 78 red blood cells are rinsed from the swabs 78 and the bloody saline then passes through the filter 79 which supports the swabs into a lower portion 81 of a swab bag 82. The bloody saline can then be pumped from the lower portion 81 of the swab bag 82 to a cell salvage machine. This embodiment has the advantage of not requiring the mechanical actuator employed in the FIG. 11b embodiment, but it does require a more complicated design of swab bag 82 since it is necessary to accommodate a shower head, support a filter and a port for connection to the cell salvage machine.

Figure 11D:
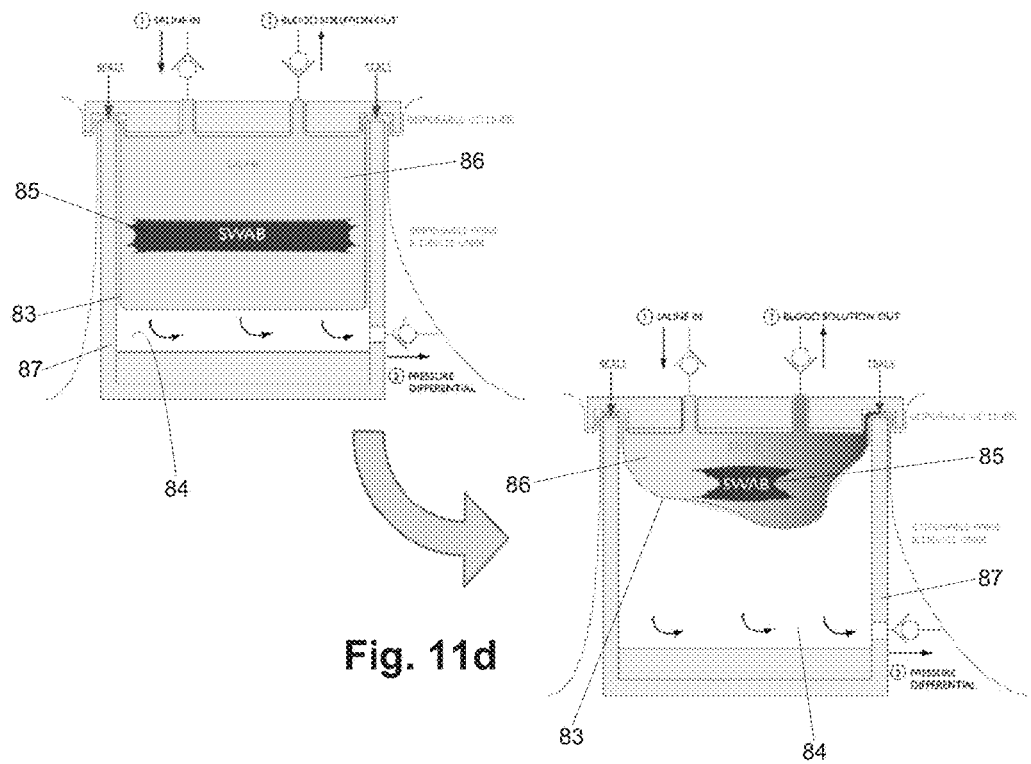
FIG. 11d is a schematic illustration of a fourth embodiment of a surgical swab washing device according to the second aspect of the present invention which may be employed in apparatus according to the third aspect of the present invention.

In FIG. 11d there is shown an embodiment in which agitation of a swab bag 83 is achieved using a pressurised space 84 below the swab bag 83. By periodically increasing and decreasing the pressure within this space 84 the swab bag 83 may be both agitated and, if desired, compressed to encourage the extraction of viable red blood cells from used swabs 85 into saline 86 within the swab bag 83. Once the desired level of agitation and compression has been achieved, negative pressure may then be applied to the contents of the bag 83 to withdrawn bloody saline to be transferred to a cell salvage machine. The space 84 subjected to increasing and decreasing pressures may be defined by a rigid container 87 within which the swab bag 83 is supported, or it may be defined by an expandable chamber (not shown), such as a balloon, retained within the rigid container 87 below the swab bag 83.

Figure 11E:
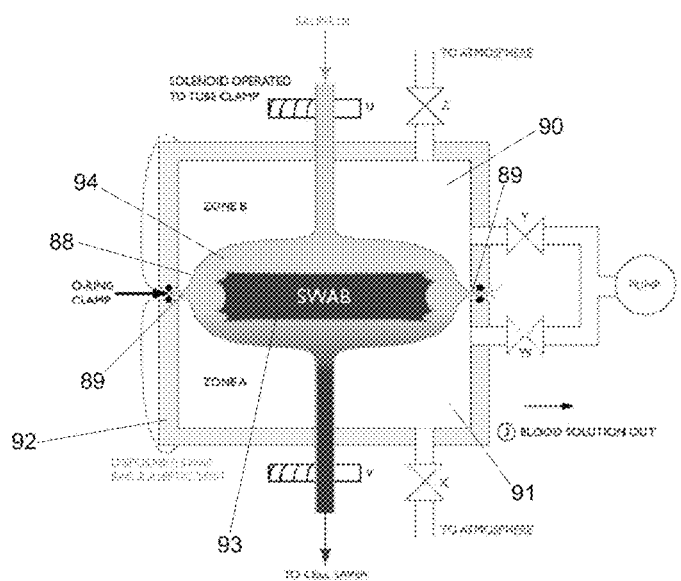
FIG. 11e is a schematic illustration of a fifth embodiment of a surgical swab washing device according to the second aspect of the present invention which may be employed in apparatus according to the third aspect of the present invention.

FIG. 11e illustrates an embodiment in which a swab bag 88 is clamped around its waist 89 so as to define pressurisable zones 90, 91 within a rigid container 92 above and below the swab bag 88. In this way the bag 88 can be agitated and/or compressed as desired to encourage viable red blood cells to be extracted from used swabs 93 into saline 94 for subsequent transfer to a cell salvage machine. By appropriate arrangement of valves, the swab bag 88 can be vibrated at varying frequencies to optimise agitation and, in turn, cell extraction. An exemplary sequence of valve operations is set out below in Table 1.

TABLE 1

| | | Pump Status | Valve Status | | | | | | |
|---|---|---|---|---|---|---|---|---|---|
| Mode | | | W | X | Y | Z | U | V | |
| Fill | | Off | Open | Open | Open | Open | Open | Shut | |
| Agitate | Pressurise chamber A | On | Open | Shut | Shut | Open | Shut | Shut | Agitation would involve alternating between these conditions every 10-15 sec to squeeze either side of swab bag and move fluid through swab |
| | Pressurise chamber B | On | Shut | Open | Open | Shut | Shut | Shut | |
| Squeeze | Pressurise chamber A & B | On | Open | Shut | Open | Shut | Shut | Open | |

Figure 11F:
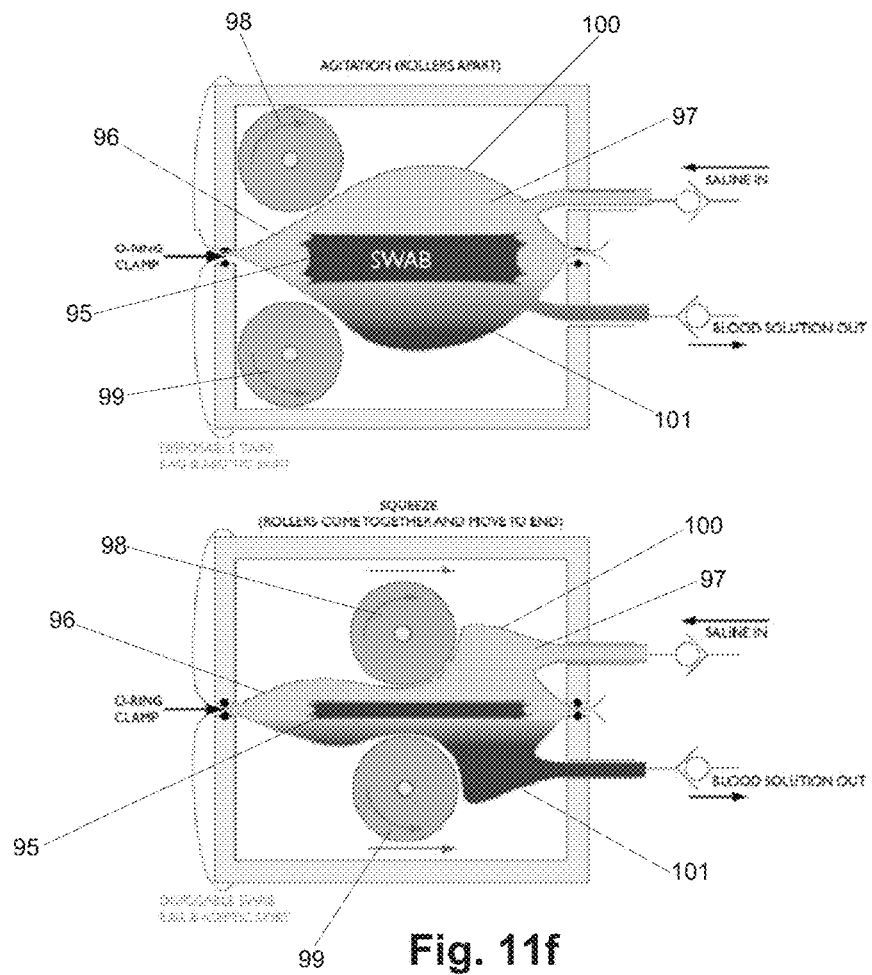
FIG. 11f is a schematic illustration of a sixth embodiment of a surgical swab washing device according to the second aspect of the present invention which may be employed in apparatus according to the third aspect of the present invention.

FIG. 11f shows a further alternative means of facilitating extraction of viable red blood cells from used surgical swabs 95. In this embodiment, agitation of swab bag 96 containing used swabs 95 and saline 97 is effected using a pair of vertically displaced rollers 98, 99 which roll across upper 100 and lower 101 surfaces of the swab bag 96 to both agitate and compress the swab bag 96 and its contents. It will be appreciated that the rollers 98,99 may be horizontally displaced from one another rather than, or in addition to being vertically displaced as shown in the illustrated embodiment. Moreover, the level of agitation and compression applied to the swab bag and its contents can be controlled by adjusting the size, rate of rotation and vertical/horizontal spacing of the rollers 98, 99.

Numerous modifications may be made to the specific elements of the preferred embodiments described above while still remaining within the scope of the present invention as defined in the appended claims. Conveniently, the apparatus according to the present invention may be considered as comprising two distinct elements: a reusable device that should be robust and provide support for the volumes of fluids used; and a disposable component comprising the swab bag, fluid reservoir and associated tubing that need not be so robust but that should still offer resistance to abrasions and vibrations. As described above, in a preferred embodiment, the disposable component incorporates tubing which will be used in combination with a peristaltic pump. Specific types of tubing can be employed for use with pumps of this kind to ensure appropriate functionality.

The swab bag is preferably highly flexible, lightweight, resistive to compression and impact and weldable. A suitable material would be a polyurethane (PU) film, such as an 80 micron clear PU film of Plation U, available from Bayer, Epurex Films Division.

The fluid reservoir is preferably flexible to allow compact packaging, clear to enable fluid levels to be seen and weldable. A suitable material would be a polyurethane (PU) film, such as a 100 micron clear PU film of Plation U, available from Bayer, Epurex Films Division.

The protective Sterile Drapes are preferably thin, lightweight, clear and capable of being sterilised. A suitable material would be a polyurethane (PU) film, such as a 25 micron clear PU film of Plation U, available from Bayer, Epurex Films Division.

The tubing connected to the receptacle and/or the reservoir is preferably clear, suitable for use with the design of pump being used, such as a peristaltic pump, suitable for single-use and weldable. A thermoplastic elastomer may be suitable, such as PureWeld XL single use tubing with an 8 mm diameter bore, available from Watson Marlow Tubing.

The pump used to transfer the saline-based wash solution between the fluid reservoir and the swab bag is preferably a peristaltic pump. Ideally, the pump should be easy to install into the apparatus and service or maintain if necessary. Preferably it is arranged to be easily associated with the tubing through which it is intended to be pumping fluids, and to provide a flow rate of at least 2 liters per minute through the tubing. A suitable peristaltic pump is a 313D OEM Peristaltic Pump available from Watson Marlow which can provide a flow rate of up to 3 liters per minute with 8 mm diameter tubing.

The upper casing containing the swab bag and/or other casings forming part of the structure of the apparatus which supports the disposable component is preferably strong, impact resistant, and made of a material or range of materials which are suitable for high-volume, cost-effective manufacture. A suitable material is the thermoplastic polymer, acrylonitrile butadiene styrene (ABS). Other components of the supporting structure should also ideally be strong and rigid, and may, for example, be formed of aluminium extrusion.

EXAMPLES

A number of test rigs were designed and manufactured to enable various approaches to swab washing to be investigated using surgical swabs soaked in human blood.

The effect of the following process parameters on the final cell yield was investigated: soaking time; agitation time; agitation frequency and amplitude; and squeezing time. A number of other factors were investigated to develop a commercially viable method and apparatus for washing surgical swabs. These other factors included: how the proposed single-use disposable bag containing the swabs interacts with the agitation and squeezing mechanisms; the simplicity of the agitation and squeezing mechanisms; the ability to set up the apparatus quickly and simply; the level of noise produced by the apparatus; the interaction of the apparatus with existing cell salvage equipment present in an operating theatre; and the impact of the apparatus on the availability of suction during surgery.

In a first set of Experiments, a series of high level tests were performed to investigate the feasibility of a range of different washing methods.

Design of Basic Test Rig

Figure 12:
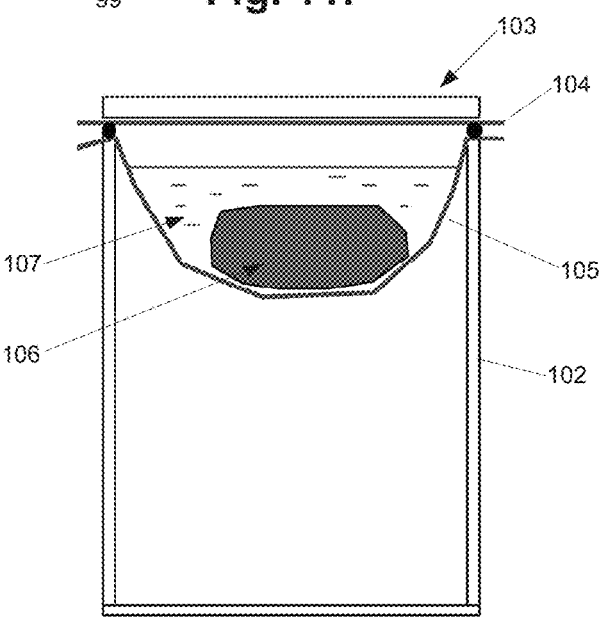
FIG. 12 is a schematic illustration of a basic test rig used to investigate the swab washing process.

The basic test rig consisted of a square aluminium frame 102 with a hinged lid 103 that enabled a flexible polyurethane liner consisting of separate upper 104 and lower 105 sections to be held within the frame 102 as shown in FIG. 12. The lower section 105 of the liner draped down into the frame 102 to form a cavity to support blood-soaked swabs 106 and saline 107. The lid 103 was clamped shut to the frame 102 to enable the cavity to be sealed. The rig was designed to ensure that the only surfaces that came into contact with the blood were the inner surfaces of the polyurethane liner. The frame 102 was designed to accommodate a variety of squeezing and agitation mechanisms below the lower section of the liner 105.

Negative Pressure Compression Method

Figure 13:
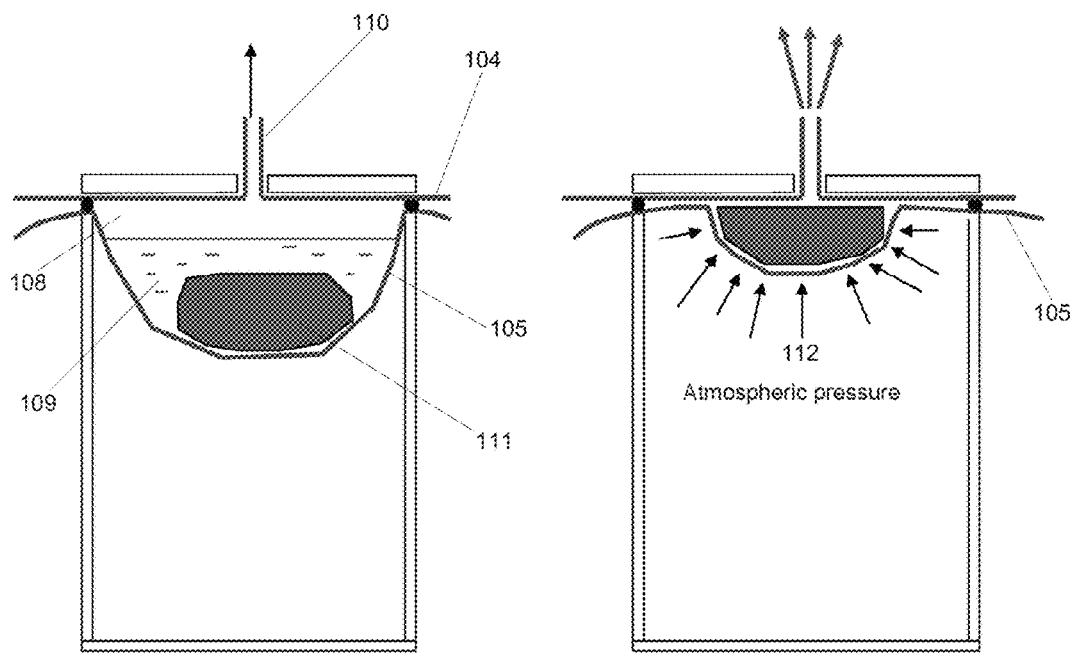
FIG. 13 is a schematic illustration of the test rig of FIG. 12 before and after the application of suction to draw fluid from within a swab washing receptacle.

The first method of squeezing the swabs that was investigated was vacuum extraction of air 108 and blood-containing saline 109 from the cavity in the lower section of the liner 105. A tube 110 attached to the upper section of the polyurethane liner 104 was connected to a centrifugal vacuum pump on a cell salvage machine as shown in FIG. 13. The air 108 and saline 109 were sucked out of the cavity containing swabs 111, which caused atmospheric pressure 112 around the lower section of the liner 105 to squeeze the swabs 111 up against a bottom surface of the aluminium lid 103. This resulted in a moist ball of compressed swabs 111 that did not drip when removed from the device. In order to avoid the swabs 111 getting sucked-up into the vacuum tube 110 and blocking it a piece of aluminium mesh (not shown) was placed over the tube 110 inlet to act as a protective grill. Variations of this method that were investigated in greater detail as described below included sucking from below the swabs 111 and using a peristaltic pump instead of a centrifugal pump.

Agitation—Pneumatic Actuation Method

Figure 14:
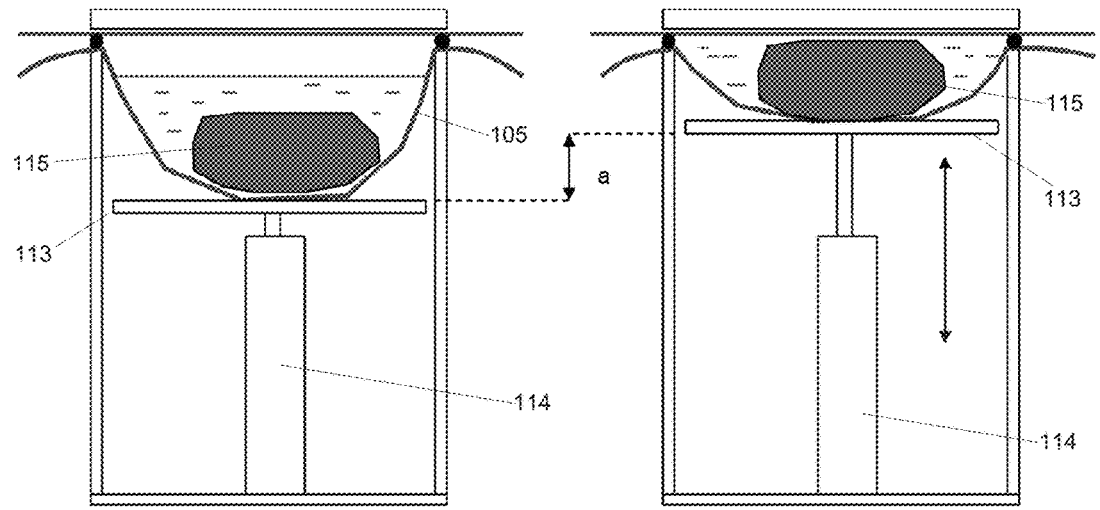
FIG. 14 is a schematic illustration of the test rig before and during agitation of the surgical swab receptacle using a pneumatically driven plate.

The first method of physically agitating the swabs that was investigated used a horizontal plate 113 mounted on a pneumatic actuator 114 underneath the lower section of the polyurethane liner 105 as shown in FIG. 14. A pneumatic actuator 114 was chosen as it enabled the following parameters to be easily varied: the agitation frequency; the amplitude of agitation (i.e. the stroke volume of the actuator=a); and the number of agitation cycles. It was also possible to use the pneumatic actuator 114 to squeeze bloody swabs 115 and to regulate the applied force (based on the air pressure in the pneumatic cylinder). The pneumatic actuator 114 was supplied via a compressor and controlled via a programmable logic controller (PLC) which enabled the above parameters to be easily varied.

Agitation—Pressurised Cavity Method

Figure 15:
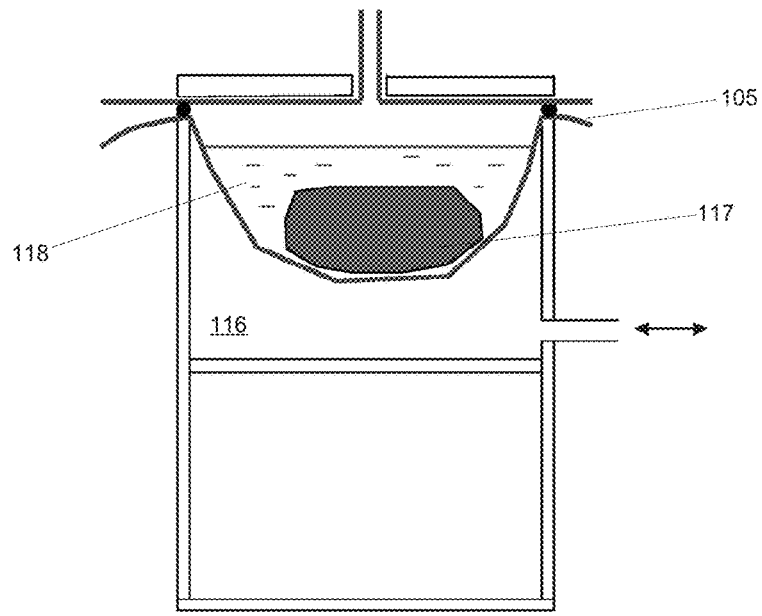
FIG. 15 is a schematic illustration of the test rig arranged to investigate the performance of a compressed air agitator.

The second agitation mechanism that was investigated replaced the pneumatic actuator with a simple pressurised cavity 116 below the lower section of the liner 105, as shown in FIG. 15. By pressurising and evacuating the cavity 116, the liner 105 rose and fell, thus agitating bloody swabs 117 in the liner 105. Since the pressurised cavity 116 did not contain any mechanical actuators (e.g. pneumatic actuators) the cavity 116 could be easily cleaned in the event of a failure of the polyurethane liner 105. Pressurisation and evacuation of the sealed cavity 116 below the liner 105 caused the liner 105 to rise and fall and resulted in the passage of saline 118 through the swabs 117. However, achieving pressurisation and evacuation of the cavity 116 quickly enough to provide significant agitation of the swabs 117 was likely to require a significant volume of compressed air, which might mean that a large and potentially noisy pump or compressor would be needed, neither of which is desirable in an operating theatre. However, this remains a viable method for washing swabs provided these problems relating to the pump/compressor could be satisfactorily addressed.

Figure 16:
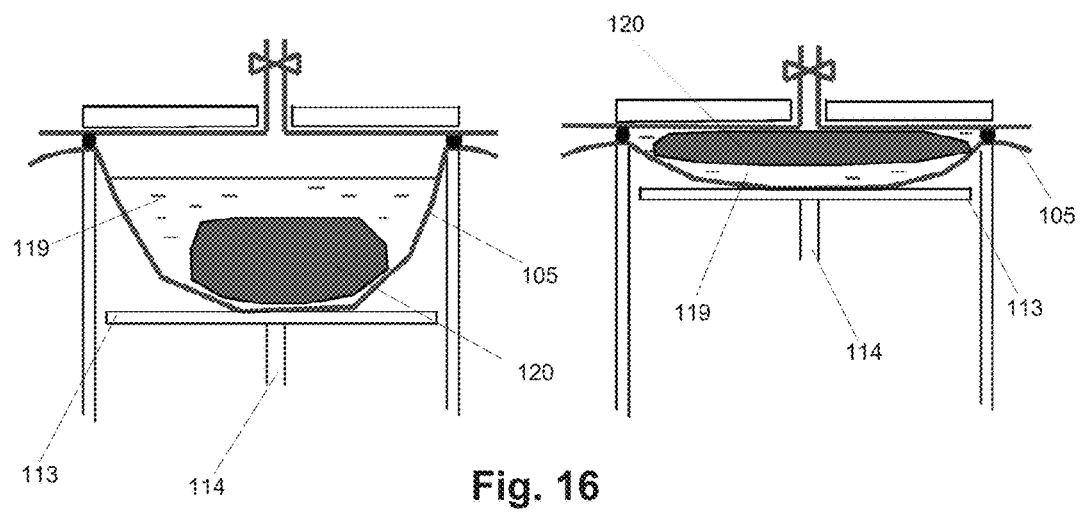
FIG. 16 is a schematic illustration of the test rig combining the features of the rig shown in FIGS. 13 and 14.
Figure 17:
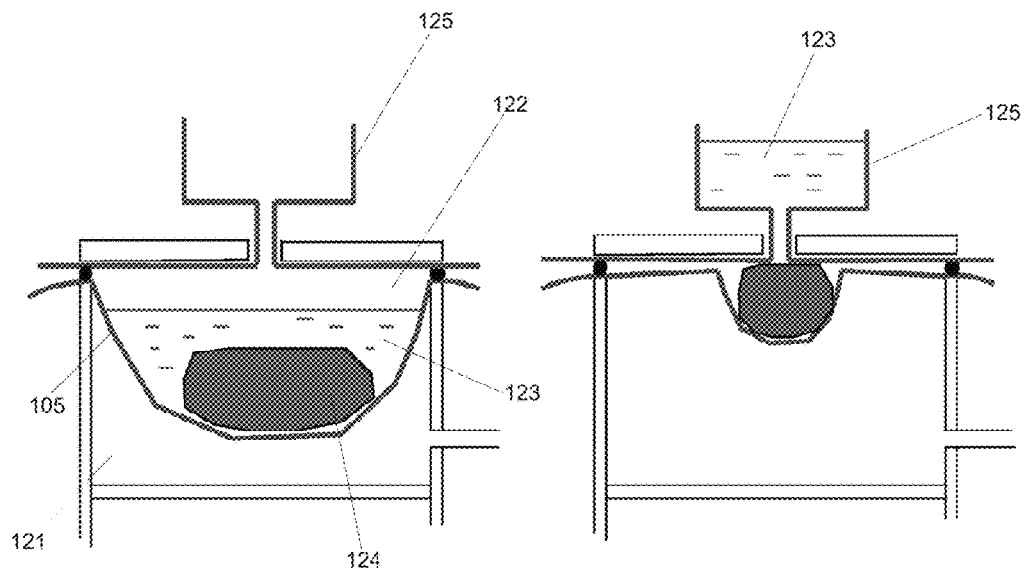
FIG. 17 is a schematic illustration of the test rig of FIG. 15 with a header-unit shown before and after pressurisation of a space below the swab receptacle.

It was also observed that there was a significant difference between the agitation effect achieved with the pneumatic actuator 114 and the pressurised cavity 116. The effect of the pneumatic actuator 114 rising was to change the shape of the liner 105 from a hemisphere to a rectangle, as shown in FIG. 16. Because there was an air space within the liner 105, the saline 119 and swabs 120 could move within this airspace. As soon as the pneumatic actuator 114 fell down, the swabs 120 and saline 110 fell back under their own weight. In contrast, with reference to FIG. 17 the effect of pressuring a sealed cavity 121 below the liner 105 was essentially the same as evacuating the liner 105. Initially all air 122 was forced out of the liner 105 followed by the saline 123. In order to achieve significant levels of fluid movement through the swabs 124 it was found to be necessary to provide a holding reservoir 125 for the saline 123 to flow into from which it could then flow back into the liner 105 when the pressure in the sealed capacity 121 was lowered. The need to provide a holding reservoir 123 and to cycle the saline 123 backwards and forwards in this way may slow down the washing process as compared to the pneumatic cylinder method.

Agitation—Vibrating Plate Method

Figure 18:
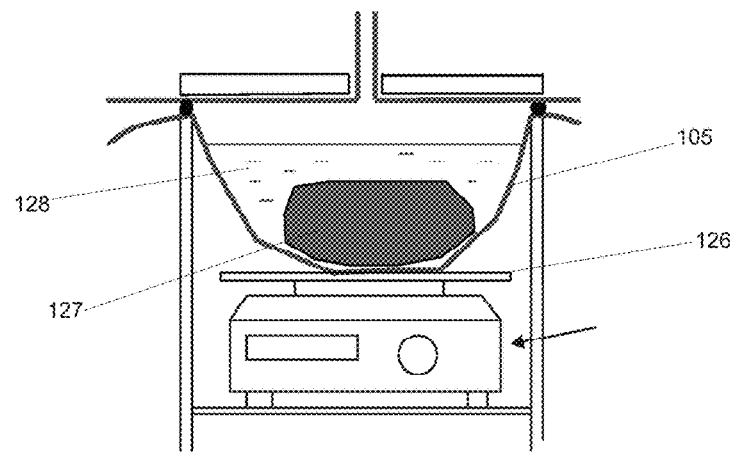
FIG. 18 is a schematic illustration of the test rig with a vibrating/oscillating plate agitator.

This method employed a vibrating plate 126 located beneath the lower section of the polyurethane liner 105 as shown in FIG. 18. The vibrating plate 126 oscillated with a circular motion through a 3 mm orbit with variable speed control: 10 to 1200 rpm. There was no significant bulk fluid movement through the swabs 127, i.e.—no sloshing from side to side. In fact the fluid movement was only apparent due to the presence of ripples on the surface of the saline 128.

In a second set of Experiments more detailed analysis of different swab washing methods was carried out.

The purpose of these experiments was to identify the efficiency of the existing manual swab washing process in terms of extraction of fluid and recovery of viable red cells.

Having set these benchmarks, the proposed mechanical methods of these processes could be investigated and compared with the established hand washing method.

1. Assessment of Swab Dry Weight

To standardise all experiments the same swab type was use to ensure consistency. These were X-ray detectable gauze swabs B.P. with tape, 22.5 cm×22.5 cm, 12 ply (Cat No. 81404/N0005, Unified Medical Products (UMP), Hampshire, UK). Packs of 5 standard swabs were weighed to ascertain the consistency of dry weight. The dry weight of an individual pack was measured five times to assess the accuracy and consistency of the balance. A second pack was then also weighed 5 times to demonstrate any variation between packs. The mean weight of pack one was 56.64+/−0.03 g. The mean dry weight of the second pack was 56.04+/−1.06 g. There was no significant difference between the dry weights of the 2 packs.

2. Investigation of Methods of Squeezing Water from Swabs

The current method of drying swabs is hand wringing. Hence we initially attempted to quantify the hand wringing process, the results of which were then used as a benchmark for the automatic system.

2.1. Efficiency of Removal of Water 2.1.1. Hand Wringing of Swabs

A pack of 5 standard surgical swabs were saturated with water. Three different individuals were then asked to wring out the swabs manually to remove the fluid. This was repeated 5 times by each individual to demonstrate the amount of variability. The mean weight of swabs after handwringing for all operators was 153.7+/−6.4 g. The mean+/−SD wrung swab weights achieved by individual operators were: 150.3 g+/−1.4g; 149.7+/−5.8 g; 161.4+/−6.4 g. There were no significant differences in the efficiency of wringing between operators 1 & 2. Operator 3 produced significantly higher wrung swab weights compared with the both operator 1 and operator 2 (p<0.05). This demonstrated the variability between individuals in undertaking the process where hand size and grip strength affect the overall result.

2.1.2. Negative Pressure Compression Method

Figure 19:
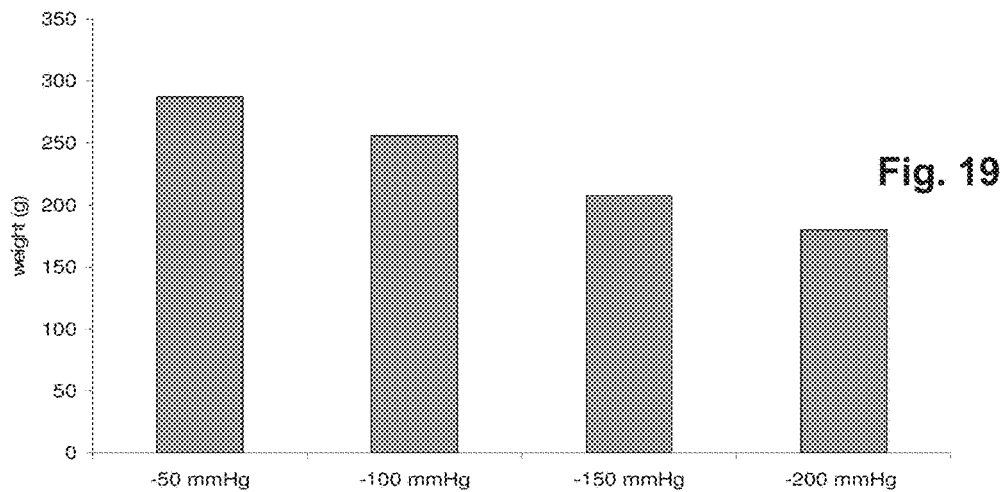
FIG. 19 is a graph to show the effect of vacuum pressure on the wet weight of swabs.

This was assessed using the basic test rig described above with an upper and lower polyurethane liner. A tube on the upper polyurethane liner was connected to the vacuum pump on the cell salvage machine. The air and saline were sucked out of the cavity containing the swabs which caused atmospheric pressure to squeeze the swabs up against the bottom surface of the aluminium lid. The effect of vacuum pressure was investigated by weighing a pack of 5 standard swabs following evacuation of a liter of water at various vacuum pressures for 5 minutes. The wet weight of the swabs decreased as the vacuum pressure increased (see FIG. 19).

As −200 mmHg consistently produced a moist ball of swabs and that a vacuum higher than this may result in cell damage, it was decided that that this would be the standard vacuum pressure for future experiments.

The basic test rig allowed for polyurethane liners to be placed with a tube outlet on the top or the bottom depending on the agitation method and any additional squeezing method to be used. We therefore tested the efficiency of squeezing when vacuum was applied to either the top or the bottom of the system.

There was no significant difference in wet weight of the swabs when applying a vacuum from the top or the bottom of the rig (−200 mmHg, 5 min).

The mean (SD) wet weight of the swabs achieved using vacuum compression was 180.0+/−4.9 g compared to 153.7+/−6.4 g for hand wringing. Whilst hand wringing is clearly more effective at extracting fluid from the swabs it was not as consistent as vacuum extraction. It is also likely that if the tests were repeated using blood, vacuum compression would result in a similar cell yield as it is necessary to apply quite a considerable force towards the end of the hand wringing process which is likely to result in greater cell damage.

2.2. Rate of Fluid Removal by Negative Pressure Compression

The rate of fluid removal from the swabs will affect the processing time for each batch of swabs. It is important that swabs can be processed within a reasonable timescale (e.g. less than 5 minutes) to ensure that the swab processing does not have a significant impact on the associated cell salvage procedures or result in a build-up of swabs during an operation.

2.2.1. Evacuation using Vacuum Applied from Above and Below 2.2.1.1. Rate of Evacuation The rate of evacuation of fluid was measured by recording the amount of time (in seconds) for set cumulative volumes of fluid to be removed from the swabs, i.e. 200, 300, 400, 500, 600, 700, 800, 900 ml respectively. This was performed with standard conditions using a pack of 5 swabs (22.5 cm×22.5 cm) placed in the test rig with a liter of water and repeated three times for each configuration. Evacuation of the water was by vacuum set at −200 mmHg for 5 minutes.

2.2.1.2. Bottom vs Top

Figure 20:
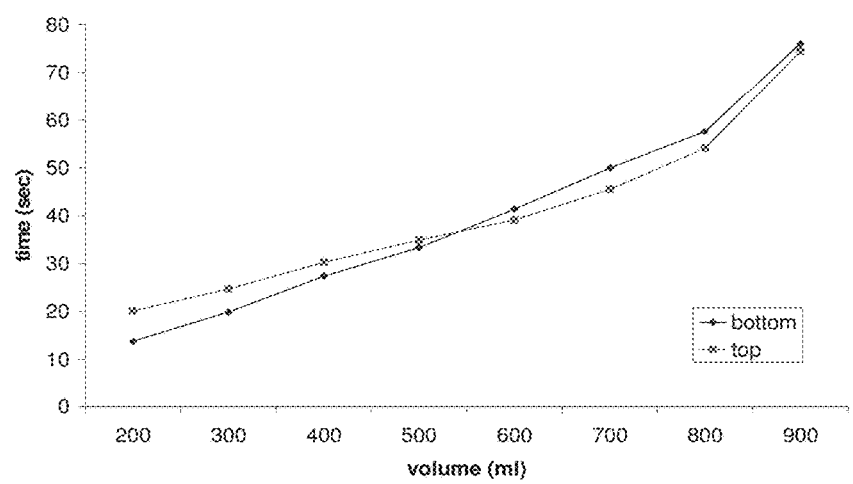
FIG. 20 is a graph to illustrate the rate when evacuation when a pressure of −200 mmHg was applied to the top or the bottom of a swab receptacle.

When full evacuation was achieved within the time frame, there was no difference in the rate of evacuation whether the outlet was at the top or the bottom of the disposable (see FIG. 20). In both configurations, however, initial test runs were abandoned when the swabs caused blockage of the outlet tubing by being sucked into the tubing. This appeared to be a random event related to the variable positioning of the swabs within the disposable in relation to the outlet. It was therefore decided to introduce some form of mechanical protection of the outlet tube to prevent this happening.

Figure 21:
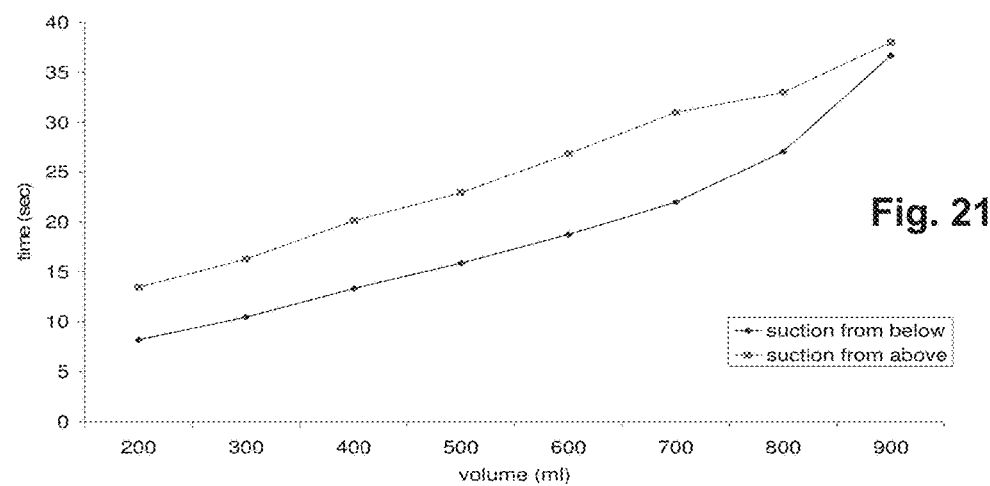
FIG. 21 is a graph to illustrate the rate of evacuation when a protective perforated cap was employed over an evacuation orifice in a swab receptacle when a vacuum was applied to the bottom or the top of the swab receptacle.

2.3. Modifications of the Outlet Tube to Prevent Blockage 2.3.1. Protective Perforated Cap The first modification evaluated was the use of a perforated protective cap positioned at the outlet tube. Evacuation rates with vacuum pressure (−200 mmHg, 5 min) applied from above and below were recorded and each test repeated three times. Introduction of the perforated cap had the desired effect with more consistent and faster rates of evacuation. There were no significant differences in the rate of evacuation (see FIG. 21) when the vacuum was applied to the top or the bottom (repeated measures analysis of variance).

2.3.2. Peritoneal Drainage Tubing

Figure 22:
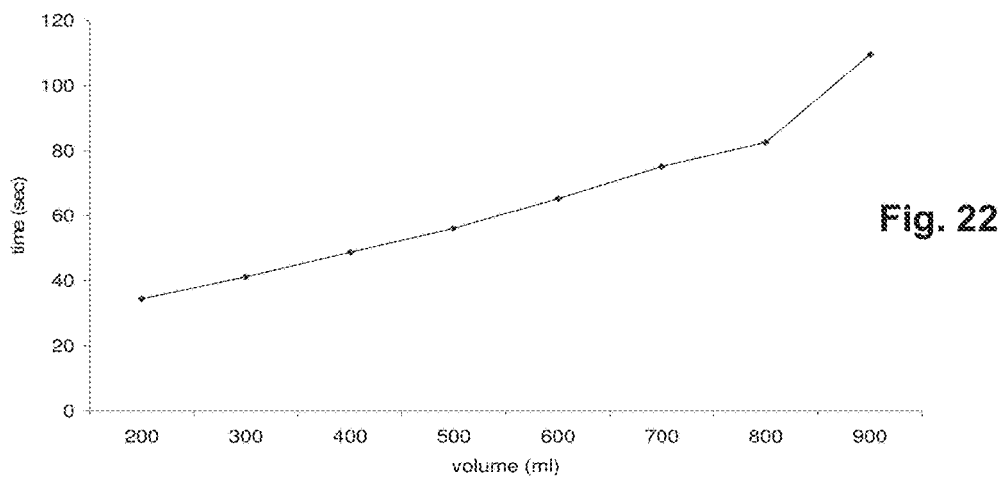
FIG. 22 is a graph showing the rate of fluid evacuation of peritoneal drainage tubing extended to the fluid outlet of a swab receptacle.

The second modification was the addition of silicone perforated drainage tubing to the internal aspect of the fluid outlet. Although the protective cap worked well, its construction of hard plastic and profile excluded the possibility of the use of a flat compression plate to aid evacuation. Evacuation rates with vacuum pressure (−200 mmHg, 5 min) applied from above were recorded and the test repeated three times. The perforated silicone tubing had the advantage of being softer and having a slimmer profile. Although this modification prevented the movement of the swabs into the outlet tube, the overall effect was to significantly prolong the process (see FIG. 22).

2.3.3. Wire Grid

Figure 23:
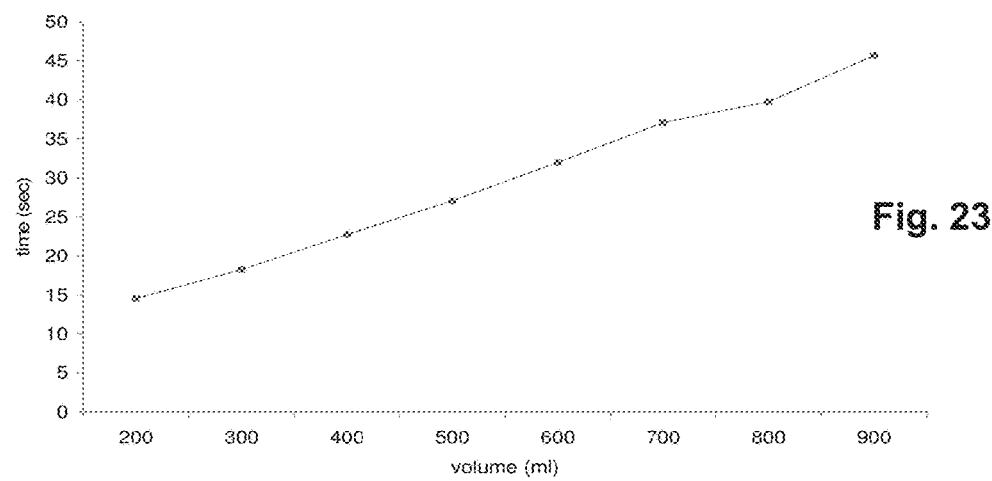
FIG. 23 is a graph showing the rate of evacuation of water from a swab receptacle with a wire grid placed over an entrance to vacuum tubing in lower section of the swab receptacle.
Figure 24:
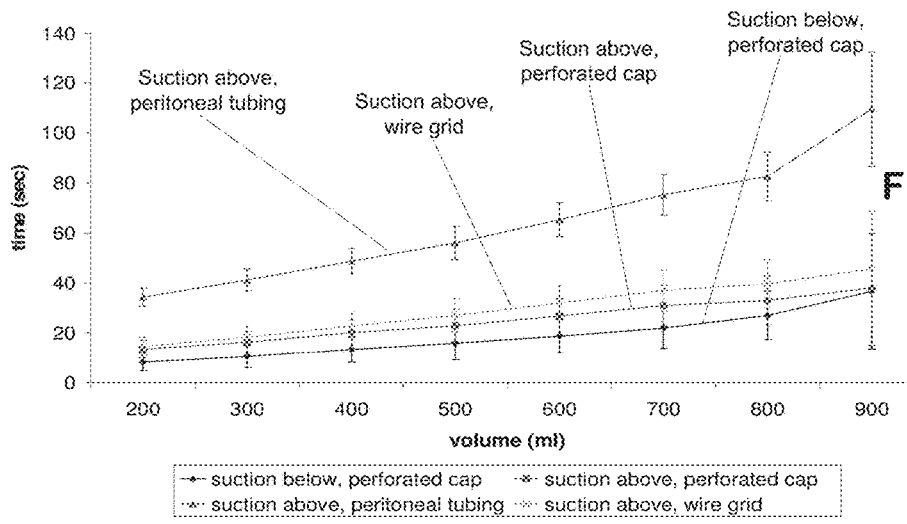
FIG. 24 is a graph comparing evacuation rates for different evacuation methods and with or without some form of filter over the entrance to the vacuum tubing.

The third modification was the addition of a flat wire grid over the internal aspect of the outlet tubing. Being flat, this had the advantage of allowing the use of the additional compressive forces exerted by the pneumatic plate in our first prototype test rig. Evacuation rates with vacuum pressure applied from above (−200 mmHg, 5 min) were recorded (see FIG. 23) and the test repeated three times. The rate of evacuation was better than the peritoneal drainage tubing but equally as good as the protective perforated cap configuration (see FIG. 24). Repeated measures analysis showed significant differences in the rate of evacuation between the perforated cap modification and the peritoneal tubing ($p<0.05$) and the wire grid modification and the peritoneal tubing ($p<0.05$). There were no significant differences between the perforated cap and the wire mesh.

2.4. Squeezing the Swabs with Vacuum and Compression

Using the wire mesh modification to protect the fluid outlet port, an investigation was then carried out to see if adding compression to the process would enhance the squeezing effect. This was achieved by using the pneumatic actuator rig described above in which a flat plate was used to push the swabs upwards against the metal lid, the pressure applied being based on the air pressure in the pneumatic cylinder (0.6bar).

2.4.1. Simultaneous Activation of Vacuum Pressure and Compression

In a first series of experiments, the pneumatic plate was activated at the same time as the vacuum being turned on. Unexpectedly this had the effect of slowing down the whole process (see FIG. 25). This was because the action of the pneumatic plate caused the swabs to take up a square flat profile and the vacuum compression was not effective against this profile.

2.4.2. Squeezing Swabs with Vacuum and Delayed Compression

A further series of tests investigated the effect of delaying the start of compression by 60 seconds. This meant that within the first minute vacuum pressure effectively removed the majority of air and fluid. The additional pressure applied by the pneumatic plate could then be exerted on the swabs to aid further removal of water. The initial use of vacuum caused the swabs to form a ball shape and the pneumatic actuator had more effect against this shape than the flat swabs. Evacuation rates with vacuum pressure applied from above (−200 mmHg, 5 min) were recorded (see FIG. 26) and the test repeated three times. Delaying the start of compression provided a significant improvement ($p<0.05$) over starting the vacuum and compression simultaneously in terms of the speed of evacuation, however, the inclusion of delayed compression conferred no additional advantage over using vacuum pressure alone (see FIG. 27) in removing water from swabs.

In all further experiments investigating red cell recovery from swabs the following standard evacuation (squeezing) parameters were adopted: wire grid protecting outlet; −200 mmHg; and 5 minute duration.

3. Development of a Red Cell Recovery Technique

The following experiments were undertaken to develop methods and apparatus capable of extracting viable red blood cells from used surgical swabs, which would then allow the extracted cells to be transferred to a cell salvage device for processing and recycling back to the patient.

3.1. Method of Assessment of Red Cell Recovery

A standard method was developed to determine red cell recovery efficiency. Donated red cell units of the same blood group where pooled and sampled to determine red cell concentration. This was achieved by undertaking a full blood count on three replicate samples of the pooled blood. A known volume (dispensed via a measuring cylinder) was then used for each experiment. In this way the total number of red blood cells in the original swabs could be calculated. Each process under investigation then produced a volume of dilute blood which was aspirated into a cell saver reservoir. The dilute blood was then processed using a Cell Saver 5 (Haemonetics UK Ltd) with a 125 ml bowl processing set. Following transfer of all of the contents of the reservoir into the spinning bowl, the machine was manually tripped to wash with 1 liter of normal saline. The resulting packed red cell product was then transferred into a reinfusion bag following the "automatic" cell saver processing parameters. The volume of product, as determined by the cell saver, was recorded ("reinfusion volume") and the contents of the bag sampled for full blood count. Using the volume and the red cell concentration it was then possible to calculate the absolute number of red cells recovered. The red cell recovery efficiency was then calculated as follows:

(Red cells recovered/Red cells loaded)×100%

The same set of cell salvage disposables were used for subsequent replicate tests within a series. As the processed blood accumulated in the reinfusion bag, basic mathematical manipulation of the data was required to determine the number of red cells added to the bag at the end of each test. This was achieved by performing a full blood count to determine red cell concentration at the end of each test. The cumulative volume was then used to calculate the total number of red cells within the reinfusion bag. The relative contribution from each test was then calculated by determining the number of red cells added to the bag each time. Sampling volumes were accounted for in the calculation and the reinfusion bag carefully agitated prior to sampling to avoid the effects of red cells settling out with gravity.

3.2. Validation of the Red Cell Recovery Method

To demonstrate the consistency of red cell recovery by the cell salvage device, 1 liter of blood with a known red cell content was processed through the cell salvage system and the number of red cells recovered in the final product measured. This was repeated several times to show any variation in processing efficiency and also with three different concentrations of red cells: $6.49 \times 10^9$/liter, $3.32 \times 10^9$/liter and $1.77 \times 10^9$/liter respectively. These concentrations were derived from adding 100 ml, 50 ml and 25 ml of donated red cells to 900 ml, 950 ml and 975 ml respectively of saline, and represent a haemoglobin concentration of approximately 2, 1 and 0.5 g/dl. These concentrations are consistent with the lower end of the range of red cell concentrations expected in the swab washing process.

The average recovery rate was 87.4% for 100 ml blood, 83.4% for 50 ml, and 88.6% for 25 ml of blood respectively (see FIG. 28). Analysis of variance revealed no significant difference in red cell recovery efficiency between red cell concentrations. The overall efficiency of red cell recovery was 86.4%.

This validation work demonstrated that inevitably some of the red cells are lost within the process, either by haemolysis or being "held-up" within the cell salvage disposable. However, consistent recovery rates were achieved establishing the method for assessing recovery efficiency rates for future experiments.

4. Investigation of Different Washing Processes 4.1. Manual Agitation and Wringing (Setting the Benchmark)

To set a benchmark, the efficiency of manual agitation and hand wringing was investigated. This was achieved by loading a standard pack of 5 swabs (22.5 cm×22.5 cm) with 100 ml of red cells of known concentration. The swabs were then placed in a liter of saline within the basic test rig within the bottom polyurethane liner. The swabs were then manually agitated for 5 minutes and then wrung out manually, with all the resulting fluid contained within the bottom disposable. The resulting red cell solution was then aspirated into the cell saver and processed as normal. This process was repeated 3 times. The number of red cells contained in the final processed product was determined and the efficiency of red cell recovery calculated. The efficiency of red cell recovery by manual agitation and hand wringing was determined as (mean+/−standard deviation) 75.8+/−8.3%.

4.2. Soaking+Negative Pressure Compression Method

The effects of soaking (without agitation) were determined by loading a pack of 5 standard swabs with 100 ml of blood of known concentration. The swabs were then placed into the basic test rig with 1 liter of saline in the lower polyurethane liner and left for 5 min. With the lid of the rig firmly in place, the fluid was then evacuated to the cell saver using vacuum pressure (−200 mmHg, 5 min) through the outlet in the upper polyurethane liner. Red cell recovery efficiency was calculated as previously described. The process was repeated 2 times. The efficiency of red cell recovery by soaking in 1 liter of saline for 5 minutes and squeezing by vacuum was determined as (mean+/−standard deviation) 55.7+/−6.6%.

4.3. Agitation–Pneumatic Actuation+Negative Pressure Compression

A standard pack of 5 swabs was loaded with 100 ml of blood of known concentration. The blood soaked swabs were then transferred to the test rig liner containing 1 liter of saline and the lid firmly closed. The swabs were then agitated by the plate raising and lowering once every 6 seconds for 5 minutes. Following this the fluid was then evacuated to the cell saver using vacuum pressure (−200 mmHg, 5 min) through the outlet in the upper polyurethane liner. Red cell recovery efficiency was calculated as previously described. The process was repeated 2 times. The efficiency of red cell recovery for agitation by pneumatic actuator and squeezing by vacuum was determined as (mean+/−standard deviation) 62.6+−7.7%.

4.4. Agitation–Pneumatic Actuation+Negative Pressure Compression+Delayed Pneumatic Compression A standard pack of 5 swabs was loaded with 100 ml of blood of known concentration. The blood soaked swabs were then transferred to the test rig liner containing 1 liter of saline and the lid firmly closed. The swabs were then agitated by raising and lowering of the plate once every 6 seconds for 5 minutes. Following this the fluid was then evacuated to the cell saver using vacuum pressure (−200 mmHg, 5 min), with the addition of compression from the actuator plate (delayed start), through the outlet in the upper polyurethane liner. Red cell recovery efficiency was calculated as previously described. The process was repeated 2 times. The efficiency of red cell recovery for agitation by pneumatic actuator and squeezing by vacuum and delayed compression was determined as (mean+/−standard deviation) 66.4+/−0.3%.

These initial tests showed that agitation with the pneumatic actuator improved the overall yield of red cells, although not sufficiently to match the efficiency of manual agitation and wringing (see FIG. 29). Due to the low number of replicates performed and the high levels of variation, however, there were no statistically significant differences between the methods investigated (ANOVA).

4.5. Effect of Changing Frequency of Pneumatic Agitation

To determine whether changing the frequency of agitation had an impact on red cell recovery efficiency a further series of experiments was performed. A standard pack of 5 swabs was loaded with 100 ml of blood of known concentration. The blood soaked swabs were then transferred to the test rig liner containing 1 liter of saline and the lid firmly closed. The swabs were then agitated by raising and lowering of the plate. The agitation parameters investigated were raising and lowering of the plate:
- a) once every second for 5 minutes
- b) once every 6 seconds for 5 minutes
- c) once every 30 seconds for 5 minutes Following agitation the fluid was then evacuated to the cell saver using vacuum pressure (−200 mmHg, 5 min), with the addition of compression from the actuator plate (delayed start), through the outlet in the upper polyurethane liner. Red cell recovery efficiency was calculated as previously described. The mean+/−SD red cell recovery efficiency was as follows:
- a) once every second for 5 minutes (n=2): 66.1+/−5.9%
- b) once every 6 seconds for 5 minutes (n=5): 75.2+/−9.7%
- c) once every 30 seconds for 5 minutes (n=2): 54.9+/−11.5%

An agitation frequency of once every 6 seconds for 5 minutes gave the optimal results and gave red cell recovery rates comparable to manual swab washing. This agitation frequency was therefore selected as standard for further experiments.

4.6. Influence of Blood Loading Volume on Red Cell ecovery Efficiency

To ascertain if the washing process was consistent when the amount of the blood varied, a further set of experiments was conducted. In these tests 25 ml, 50 ml & 100 ml of blood respectively as loaded onto standard packs of 5 swabs. Washing was by agitation with the pneumatic agitator (frequency of agitation once every 6 seconds for 5 mins), squeezing by vacuum and delayed compression. The mean+/−SD red cell recovery efficiency was as follows:

25 ml blood loading volume (n=7): 71+/−22%
50 ml blood loading volume (n=3): 63.7+/−5.1%
100 ml blood loading volume (n=5): 75.2+/−9.7%

Although there was a lot of variation, the loading volume of blood (within the ranges investigated) did not appear to influence the efficiency of red cell recovery from the swabs.

4.7. Determining the Effect of the Temperature of the Saline Wash

All previous experiments had been performed with 1 liter of saline in the rig at room temperature. It is common practice within the manual swab washing process to set up the swab washing bowl with saline warmed to 37° C. As there is no active heating of the bowl within the theatre environment, this temperature inevitably drops to room temperature over the duration of the operation. We investigated the effect of saline temperature in our system by warming saline to 37° C. in an incubator prior to use.

A standard pack of 5 swabs was loaded with 25 ml of blood of known concentration. The blood soaked swabs were then transferred to the test rig liner containing 1 liter of warmed saline and the lid firmly closed. The swabs were then agitated by raising and lowering of the plate once every 6 seconds for 5 minutes. Following this the fluid was then evacuated to the cell saver using vacuum pressure (−200 mmHg, 5 min), with the addition of compression from the actuator plate (delayed start), through outlet in the upper polyurethane liner. Red cell recovery efficiency was calculated as previously described. The process was repeated 3 times. The mean+/−SD red cell recovery efficiency with warm saline was 72.7+/−13.1%. This was not significantly different from the yield achieved with saline at room temperature.

4.8. Agitation–Vibrating Plate+Negative Pressure

Using the basic rig, the effect of an oscillating platform on red cell recovery was investigated. This was achieved by using an orbital shaker (Corning® LSETM Digital Microplate Shaker, Corning Inc, Mass., USA). This shaker oscillates a platform with a circular motion through a 3 mm orbit with variable speed control: 10-1200 rpm. For these experiments 50 ml of blood was loaded onto standard packs of 5 swabs. The shaker was situated under the bottom polyurethane liner containing 1 liter of saline such that the platform of the shaker fully supporting the weight of the liner containing saline up to a standard depth. The blood soaked swabs were placed in the rig and the lid sealed. The swabs were then oscillated at a set speed for 5 minutes duration. The speeds investigated were: 100 rpm, 250 rpm, 750 rpm, and 1000 rpm. The swabs were then squeezed and the fluid evacuated by applying a vacuum pressure of −200 mmHg for 5 minutes. Red cell recovery efficiencies were calculated as previously described. The experiment was repeated three times at each oscillating speed. The oscillating platform produced recovery rates in excess of 80% (see FIG. 30) when the rate of oscillation was at least 750 rpm. These were the best recovery rates recorded and are at least equivalent to, if not better than, those achievable by a manual swab washing process.

4.9. Varying Other Parameters

To optimise the process and look at other potential influences on the washing efficiency of the pneumatic agitator, the following variables were modified:
- a) amplitude of agitation increased to a maximum of 88 mm (height between lowest and highest point), n=3
- b) separating the swabs individually before adding to the rig, n=3
- c) using a single large swab (44.5 cm×44.5 cm) instead of a standard pack of 5 swabs (22.5 cm×22.5 cm), n=3

In all of these experiments the following parameters were constant: blood load volume—50 ml; saline wash volume—1 liter; agitation frequency—once every 6 seconds for 5 minutes; and evacuation by vacuum, −200 mmHg from top of liner for 5 minutes with delayed compression.

Modifying these variables did not significantly change the efficiency of the washing process (see FIG. 31).

5. Effect of Mechanical Processes on Red Cell Morphology

Throughout the testing process blood samples were routinely taken for examination by light microscopy. Red cell morphology of the recovered red cells, after mechanical washing and cell salvage processing, consistently showed no significant change when compared to pre-process samples (see FIG. 32).

CONCLUSIONS

It is possible to automatically wash swabs within a single use disposable sterile field and achieve red blood cell yields in excess of the yields achieved with manual swab washing. Importantly, an automatic swab washing device can result in red blood cell yields in excess of 75%, the benchmark demonstrated for manual swab washing.

A low amplitude vibratory washing system achieved the greatest red cell yields (up to 82%) and these yields increased as the frequency of vibration increased. A vacuum based system was a very effective method to squeeze the swabs and resulted in a compact package of moist swabs that could be easily extracted from the device without dripping blood.

It will be understood that numerous modifications can be made to the embodiments of the invention described above without departing from the underlying inventive concept and that these modifications are intended to be included within the scope of the invention. For example, it will be appreciated that features of the different preferred embodiments of the present invention described above can be combined together in numerous different arrangements to suit a particular application while still being in accordance with the present invention.

The invention claimed is:

1. A method for washing surgical swabs to extract viable red blood cells from said swabs, the method comprising:
    contacting at least one swab retaining viable red blood cells with a saline-based wash solution in a flexible receptacle under sterile conditions; and
    effecting automated compression and automated agitation of the flexible receptacle containing said at least one swab, saline-based wash solution and red blood cells to facilitate extraction of viable red blood cells from said at least one swab into the saline-based wash solution,
    wherein automated agitation of the flexible receptacle is effected at least before automated compression of the flexible receptacle; and
    wherein said flexible receptacle has a non-compressed position prior to automated compression, and a compressed position during automated compression in which a lower section of the flexible receptacle squeezes the at least one swab.

2. A method according to claim 1, wherein the method comprises automated compression of the receptacle containing said at least one swab, saline-based wash solution and red blood cells by the extraction of fluid from within said receptacle.

3. A method according to claim 1, wherein the method comprises automated compression of the receptacle containing said at least one swab, saline-based wash solution and red blood cells by the application of a physical force to at least one exterior surface of the receptacle.

4. A method according to claim 3, wherein said physical force is generated by at least one driven member configured to contact said at least one exterior surface of the receptacle.

5. A method according to claim 4, wherein said at least one driven member is selected from the group consisting of: a pneumatically driven plate positioned below the receptacle configured to be driven against said at least one exterior surface of the receptacle; at least one roller configured to be driven over said at least one exterior surface of the receptacle; and a pair of rollers configured to be driven over opposing exterior surfaces of the receptacle.

6. A method according to claim 3, wherein said physical force is generated by increasing the pressure of a fluid within at least one sealed space located adjacent to the receptacle.

7. A method according to claim 1, wherein the method comprises automated agitation of the receptacle containing said at least one swab, saline-based wash solution and red blood cells by repeated application of a physical force to at least one exterior surface of the receptacle.

8. A method according to claim 7, wherein said physical force is generated by at least one driven member configured to repeatedly contact said at least one exterior surface of the receptacle.

9. A method according to claim 8, wherein said at least one driven member is selected from the group consisting of: a pneumatically driven plate positioned below the receptacle, the plate configured to be repeatedly driven towards and away from said at least one exterior surface of the receptacle; an oscillating plate positioned so as to contact the receptacle, the plate configured to oscillate repeatedly while contacting said at least one exterior surface of the receptacle; at least one roller configured to be repeatedly driven over said at least one exterior surface of the receptacle; and a pair of rollers configured to be repeatedly driven over opposing exterior surfaces of the receptacle.

10. A method according to claim 7, where said physical force is generated by increasing the pressure of a fluid within at least one sealed space located adjacent to the receptacle.

11. A method according to claim 1, wherein the automated compression comprises removing saline-based wash solution containing red blood cells from within the flexible receptacle.

12. The method according to claim 11, wherein the automated compression comprises creating negative pressure within the flexible receptacle that causes the flexible receptacle to compress.

13. The method according to claim 12, wherein the amount of negative pressure within the flexible receptacle is increased during automatic compression at a rate selected to minimize damage to the red blood cells.

14. A method for washing surgical swabs in an apparatus to extract viable red blood cells from said swabs, the method comprising:
    pumping saline-based wash solution into a flexible receptacle;
    contacting at least one swab retaining viable red blood cells with the saline-based wash solution in the flexible receptacle under sterile conditions;
    effecting automated agitation of the flexible receptacle containing said at least one swab, saline-based wash solution and red blood cells to extract viable red blood cells from said at least one swab and create saline-based wash solution containing red blood cells; and
    effecting automated compression of the flexible receptacle, wherein the automated compression comprises removing saline-based wash solution containing red blood cells from within the flexible receptacle and creating negative pressure within the flexible receptacle that causes the flexible receptacle to compress.

15. The method of claim 14, wherein, during the automated compression, the flexible receptacle compresses against the at least one swab and forces the at least one swab against a lid of the apparatus.

16. The method according to claim 14, wherein the amount of negative pressure within the flexible receptacle is increased during automatic compression at a rate selected to minimize damage to the red blood cells.

* * * * *